(12) United States Patent
Bornzin et al.

(10) Patent No.: US 11,511,108 B2
(45) Date of Patent: Nov. 29, 2022

(54) SYSTEMS AND METHODS FOR IMPLANTING A MEDICAL DEVICE

(71) Applicant: Pacesetter, Inc., Sylmar, CA (US)

(72) Inventors: Alexander R. Bornzin, Los Angeles, CA (US); Gene A. Bornzin, Santa Monica, CA (US); Zoltan Somogyi, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 16/907,515

(22) Filed: Jun. 22, 2020

(65) Prior Publication Data

US 2021/0393947 A1 Dec. 23, 2021

(51) Int. Cl.
*A61N 1/05* (2006.01)

(52) U.S. Cl.
CPC ........... *A61N 1/057* (2013.01); *A61N 1/0563* (2013.01); *A61N 2001/058* (2013.01)

(58) Field of Classification Search
CPC ...... A61N 1/0563; A61N 1/057; A61N 1/058; A61N 1/39622; A61N 1/3627; A61N 1/3622; A61N 1/056; A61N 1/3624; A61N 1/37512; A61N 1/0573; A61N 2001/0578; A61N 2001/058; A61N 1/0587; A61N 1/362; A61N 1/36842; A61N 1/3686; A61N 2001/0582
See application file for complete search history.

(56) References Cited

U.S. PATENT DOCUMENTS

| 4,467,817 | A | * | 8/1984 | Harris | A61N 1/057 607/122 |
| 4,583,543 | A | * | 4/1986 | Peers-Trevarton | A61N 1/3752 607/1 |
| 7,287,995 | B2 | | 10/2007 | Stein et al. | |
| 2005/0043771 | A1 | * | 2/2005 | Sommer | H01R 13/5224 607/37 |

(Continued)

OTHER PUBLICATIONS

Lamas et al "Ventricular Pacing or Dual-Chamber Pacing for Sinus-Node Dysfunction" The New England Journal of Medicine; 2002; 9 pages.

(Continued)

*Primary Examiner* — Carl H Layno
*Assistant Examiner* — Anh-Khoa N Dinh
(74) *Attorney, Agent, or Firm* — The Small Patent Law Group LLC; Dean D. Small

(57) ABSTRACT

Systems and methods are provided for implanting a medical device. An implantable lead comprises a lead body, with electrodes positioned at the distal end and a lead connector positioned at the proximal end. The lead body has a body outer envelope configured to fit within a lumen of an introducer sheath and the lead connector has a connector outer envelope configured to fit within the lumen of the introducer sheath. A lead adaptor is configured to interconnect the implantable lead and the pulse generator. The lead adaptor has an insertable connector that includes mating contacts and an adaptor cavity that includes cavity contacts. The cavity contacts are positioned to engage the lead con- (Continued)

tacts of the lead connector when the lead connector is inserted into the adaptor cavity. The insertable connector is configured to be inserted into the connector cavity of the pulse generator.

24 Claims, 12 Drawing Sheets

(56) References Cited

U.S. PATENT DOCUMENTS

2008/0319499 A1* 12/2008 Zhu .................. A61N 1/37
                     607/9
2015/0133953 A1* 5/2015 Seifert ............ A61N 1/0504
                     606/129

OTHER PUBLICATIONS

Wilkoff et al. "Dual-Chamber Pacing or Ventricular Backup Pacing in Patients with an Implantable Defibrillator" American Medical Association; 2002; 9 pages.

* cited by examiner

SYSTEMS AND METHODS FOR IMPLANTING A MEDICAL DEVICE

BACKGROUND

Embodiments of the present disclosure relate generally to systems and methods for implanting medical devices within a patient, and more particularly to delivery systems for implanting one or more leads.

Cardiac pacemakers and implantable cardioverter-defibrillators (ICD) use insulated wires (called leads) to monitor the heart and to also deliver electrical signals or shocks. Various techniques exist for implanting cardiac pacemakers, ICDs, and other medical devices, and each technique may use a set of tools designed for that technique. To position a lead, for example, a number of elongated tools (e.g., needles, guidewires, sheaths, and stylets) are inserted into the body. In many cases, the lead is inserted through the lumen of an introducer sheath. After the lead is positioned relative to the heart, the introducer sheath is removed.

Removing the introducer sheath without inadvertently displacing the lead can be challenging. The leads are thin and, when finally positioned, may have a number of bends or twists along its path. Furthermore, the proximal end of the lead includes a connector that is larger than the diameter of the sheath's lumen. To address this issue, splittable or peelable sheaths are used. The sheaths are split and separated from each other as the sheaths are withdrawn from the body. As such, the sheaths may be removed while avoiding the connector at the proximal end of the lead.

Although these splittable/peelable sheaths are useful, the withdrawal process can still be challenging, especially for certain procedures. More recently, the His-Purkinje system has been proposed as a physiologic substitute for right-ventricle pacing. Recent clinical trials demonstrated an increased risk of hospitalization for heart failure (HF) in patients having a high burden of right-ventricle (RV) pacing and consequently an increased risk of arrhythmias. His-bundle pacing (HBP) uses native conduction pathways and could prevent the negative effects of RV pacing and promote ventricular synchrony.

It remains challenging, however, to locate the His and achieve true selective capture. During this procedure, a slittable introducer sheath with a dilator is advanced over a guide wire until the dilator end reaches the atrium or right ventricle. With the introducer sheath in place, the implanter removes the guidewire and the dilator and advances a pacing lead through the lumen of the introducer sheath. In some cases, the pacing lead accepts a stylet to provide rigidity and push-ability to the lead. After the pacing lead is positioned, the introducer sheath is slit and removed, leaving the lead in place.

As discussed above, the implanter is careful when withdrawing the introducer sheath so that the introducer sheath does not strike the connector at the proximal end and dislodge the lead from its desired position. If the lead is dislodged, the lead-implantation procedure must begin again. Repeating the process increases the risk of infection in addition to other complications that may arise during such medical procedures.

SUMMARY

In accordance with embodiments herein, a system is provided. The system includes an implantable lead comprising a lead body having a distal end and a proximal end. The implantable lead has electrodes positioned at the distal end and has a lead connector positioned at the proximal end. The lead connector includes lead contacts that are communicatively coupled to the electrodes positioned at the distal end. The lead body has a body outer envelope configured to fit within a lumen of an introducer sheath and the lead connector has a connector outer envelope configured to fit within the lumen of the introducer sheath. A pulse generator has a connector cavity. The lead adaptor is configured to interconnect the implantable lead and the pulse generator. The lead adaptor has an insertable connector that includes mating contacts and an adaptor cavity that includes cavity contacts. The cavity contacts are positioned to engage the lead contacts of the lead connector when the lead connector is inserted into the adaptor cavity. The insertable connector is configured to be inserted into the connector cavity of the pulse generator.

Optionally, the body outer envelope may be defined by a first dimension and the connector outer envelope may be defined by a second dimension that is not greater than the first dimension. The body outer envelope may be defined by an outer radius extending from a central longitudinal axis to an outer surface of the lead body. The insertable connector may have an insertable outer envelope that may be larger than the lumen of the introducer sheath. The system may comprise the introducer sheath, the lead connector and the distal end of the lead body being slidable within the lumen of the introducer sheath. The system may comprise low-friction material disposed between an interior surface of the introducer sheath and the lead body.

Optionally, the lead adaptor may have an adaptor body and a strain-relief segment coupled to a receiving end of the adaptor body. The adaptor body and the strain-relief segment may define respective portions of the adapter cavity. The strain-relief segment may be configured to at least partially resist bending forces delivered by the implantable lead. The lead body may include a fixation anchor attached to the distal end and may be configured to be implanted within tissue. The system may further comprise a holding stylet configured to engage the lead body when the introducer sheath is withdrawn and diminish withdrawing forces that pull the fixation anchor away from the tissue.

In accordance with embodiments herein, a system is provided. The system includes an introducer sheath having a lumen. The system includes an implantable lead comprising a lead body having a distal end and a proximal end. The implantable lead has electrodes positioned at the distal end and has a lead connector positioned at the proximal end. The lead connector includes lead contacts that are communicatively coupled to the electrodes positioned at the distal end. The lead body has a body outer envelope configured to fit within the lumen of the introducer sheath and the lead connector has a connector outer envelope configured to fit within the lumen of the introducer sheath. A lead adaptor is configured to interconnect the implantable lead and a pulse generator. The lead adaptor has an insertable connector that includes mating contacts and an adaptor cavity that includes cavity contacts. The cavity contacts are positioned to engage the lead contacts of the lead connector when the lead connector is inserted into the adaptor cavity. The insertable connector is configured to be inserted into a connector cavity of the pulse generator.

Optionally, the body outer envelope may be defined by a first dimension and the connector outer envelope may be defined by a second dimension that is not greater than the first dimension. The body outer envelope may be defined by an outer radius extending from a central longitudinal axis to an outer surface of the lead body. The insertable connector may have an insertable outer envelope that may be larger than the lumen of the introducer sheath. The proximal and distal ends of the lead body may be slidable within the lumen of the introducer sheath. The system may comprise low-friction material disposed between an interior surface of the introducer sheath and the lead body.

Optionally, the lead adaptor may have an adaptor body and a strain-relief segment coupled to a receiving end of the adaptor body. The adaptor body and the strain-relief segment may define respective portions of the adapter cavity. The lead body may include a fixation anchor attached to the distal end and may be configured to be implanted within tissue. The system may further comprise a holding stylet configured to engage the lead body when the introducer sheath is withdrawn and diminish withdrawing forces that pull the fixation anchor away from the tissue. The lead body may be a lumen-less lead body. The holding stylet may be configured to engage the proximal end of the lead body. The lead body may have a lumen. The holding stylet may be configured to be inserted through the lumen of the lead body and engage an interior of the lead body at or near the distal end.

In accordance with embodiments herein, a method is provided. The method provides providing an introducer sheath has a proximal sheath end and a distal sheath end. The introducer sheath has a lumen that extends between the proximal and distal sheath ends. The method inserts the introducer sheath into a patient. The method advances an implantable lead through the lumen of the introducer sheath. The implantable lead includes a lead body having a distal lead end and a proximal lead end. The implantable lead has electrodes positioned at the distal lead end and has a lead connector positioned at the proximal lead end. The lead body has a body outer envelope configured to fit within the sheath lumen and the lead connector has a connector outer envelope configured to fit within the sheath lumen. The method positions the distal lead end of the implantable lead at a desired position within the patient. The method engages the lead body with a holding stylet. The method removes the introducer sheath such that an interior surface of the introducer sheath slides along an exterior surface of the implantable lead. The holding stylet engages the lead body when the introducer sheath is withdrawn and diminishes withdrawing forces that pull the distal lead end of the implantable lead away from the desired position. The method slides the distal sheath end over the proximal lead end such that the introducer sheath clears the proximal lead end.

Optionally, the lead body may include a fixation anchor attached to the distal lead end. The positioning the distal lead end may include implanting a fixation anchor within tissue.

DETAILED DESCRIPTION

Figure 2:
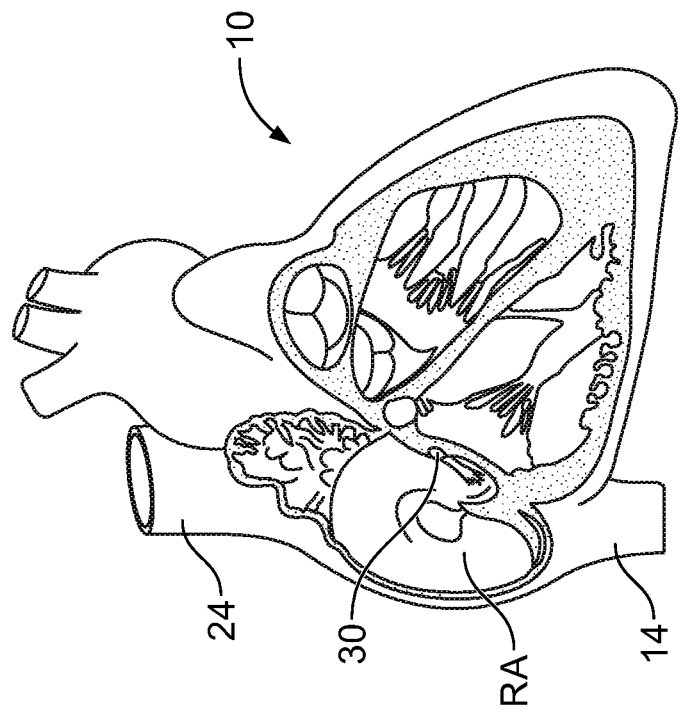
FIG. 2 is another schematic view of the heart showing a location of the His bundle relative to other cardiac structures.

Embodiments set forth herein include delivery systems for implantable medical devices (IMDs), assemblies or kits of the delivery systems or IMDs, and methods for making and using the same. Particular embodiments are implemented in connection with a His-bundle pacing (HBP) strategy or system in which cardiac tissue is stimulate at or near the His bundle. Although embodiments may be described in relation to HBP, it should be understood that embodiments may be used in connection with a variety of IMDs and medical procedures delivering or using the IMDs. Such procedures may include implanting or extracting leads.

An IMD is a medical device which is intended to be totally or partially introduced into a body (human or animal) and remain in the human body after the procedure. An IMD may include a single component or a system of components that interact to achieve a desired performance. IMDs typically include at least one active component that perform monitoring and/or therapy functions through electrical energy. Non-limiting examples of IMDs include a cardiac monitoring device, a pacemaker, cardioverter, cardiac rhythm management device, defibrillator, neurostimulator, and the like. Many IMDs may provide multiple functions and include implantable cardioverter defibrillators (ICDs) and implantable cardiac resynchronization therapy/defibrillator devices (CRT-Ds).

IMDs often include a control device (e.g., pulse generator) and one or more other components that coordinate with the control device. For example, cardiac IMDs often include a pulse generator and one or more leads. The pulse generator has a power source and electronic circuitry that is configured to monitor the heart. The pulse generator may include one or more processors that implement programmed instructions (e.g., software or firmware) stored in memory of the pulse generator. For example, the pulse generator may be programmed to provide output stimuli (e.g., signals for pacing or a shock) through the lead or leads.

A lead includes one or more insulated electrical conductors that are intended to transfer electrical energy along a length of the lead. For example, the lead may transfer output stimuli from the pulse generator or transmit depolarization potentials from cardiac tissue to a sensing circuit of the pulse generator. A lead typically includes a lead body having an elongated flexible tube or sleeve comprising, for example, a biocompatible material (e.g., polyurethane, silicone, etc.). The lead (or lead body) has a distal end and a proximal end. As used herein, the terms "proximal" and "distal," when used in reference to a lead (or other elongated instruments, such as an introducer sheath, catheter, guidewire, or stylet) are to be understood in relation to delivering and implanting a medical device. During an implantation procedure, "proximal" is to be understood as relatively close to the implanter and "distal" is to be understood as relatively far away from the implanter. After the implantation, a proximal end of a lead is coupled to a pulse generator, and a distal end of the lead is positioned adjacent to tissue (e.g., cardiac or nerve tissue).

The lead body may include a single lumen (or passage) or multiple lumen (or passages) within the flexible tube. A lead may have multiple electrical conductors (not shown) that electrically couple electrode(s) of the lead to the pulse generator. The electrical conductors may be cabled conductors coated with PTFE (poly-tetrafluoroethylene) and/or ETFE (ethylenetetrafluoroethylene). The electrical conductors are terminated to the respective electrode. The lead body may be configured for receiving a guide wire or stylet that enable positioning of the lead.

The lead may include one or more electrodes or one or more contacts through which electrical energy may leave or enter the conductors of the lead. Electrodes may be positioned adjacent to tissue for monitoring or providing therapy thereto. The lead connector also includes one or more contacts that are communicatively coupled to the one or more electrodes. The lead adaptor and the pulse generator are also described as including contacts. To more readily distinguish electrodes and contacts, the electrodes can be described as being positioned at the distal end and the contacts can be described as being positioned at the proximal end of the lead or as part of a lead adaptor or a pulse generator.

Various types of electrodes and contacts exist, including tip electrodes or contacts, ring electrodes or contacts, contact pads, patch electrodes, spring electrodes, or porous electrodes. Electrodes and contacts may also have a variety of configurations or patterns (e.g., unipolar, bipolar or multipolar, array, etc.). In particular embodiments, the electrodes/contacts may be arranged according to international standard 1 (IS-1) that are used for low-voltage applications. The configuration may be unipolar or bipolar. A largest dimension of an IS-1 lead connector is 3.2 mm.

The lead adaptor enables an electrical and mechanical connection between the lead connector and the pulse generator. The lead adaptor may be used to upsize or downsize the lead connector in order to mate with the pulse generator. Optionally, the lead adaptor may also function as a lead extender that effectively increases the length of the lead.

Leads also include a lead connector positioned at the proximal end. The lead connector provides an electrical connection between the one or more electrodes of the lead and the one or more contacts of a control device (e.g., pulse generator). As described herein, the lead connector can also mate with a lead adaptor. The lead adaptor may then mate with the pulse generator to electrically connect the electrodes to the pulse generator and mechanically connect the lead to the pulse generator.

A lead may be delivered and positioned relative to tissue using an introducer sheath. An introducer sheath is a tube or cannula that is introduced into the body (e.g., through the vascular system, for example), typically over another elongated instrument, such as a needle, dilator, or guidewire. The introducer sheath includes a lumen that permits passage of other elongated instruments, such as the lead. The introducer sheath may form part of a delivery system (or kit) that includes one or more other elongated instruments, such as a needle, a guidewire, a syringe, a dilator, and one or more other sheaths. In particular embodiments, the introducer sheath is non-splittable or non-peelable. In particular embodiments, the introducer sheath is an intravascular sheath having at least one lumen.

Figure 1:
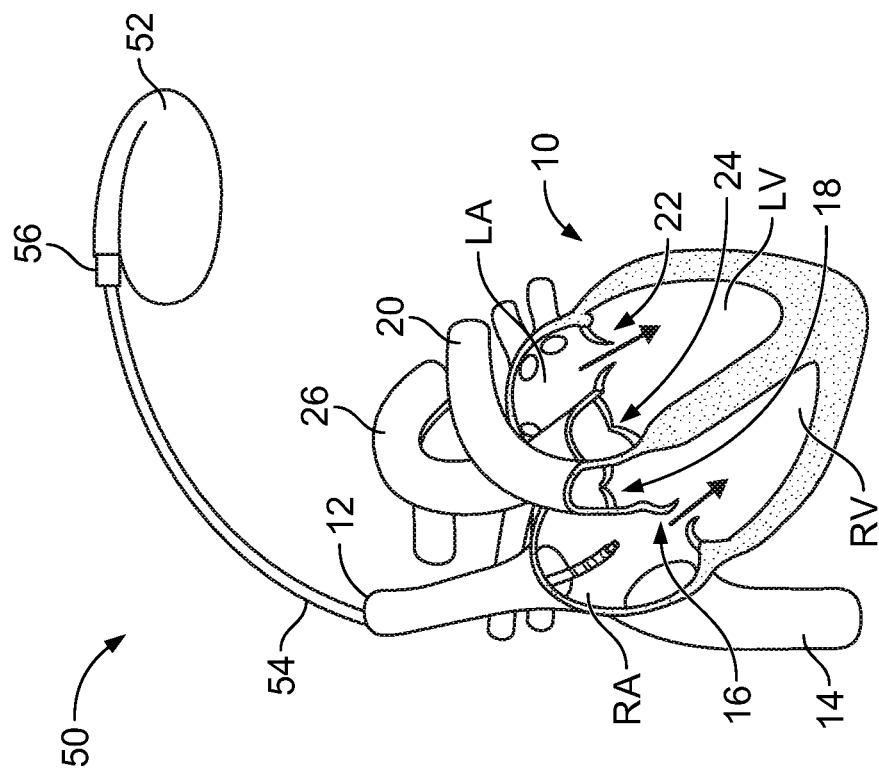
FIG. 1 is a schematic view of a heart illustrated in relation to an implantable medical device (IMD) formed in accordance with an embodiment that includes an implantable lead and a pulse generator interconnected by a lead adaptor.

FIG. 1 illustrates a schematic cutaway view of a heart 10 relative to an IMD 50. The heart 10 includes a right atrium RA, a right ventricle RV, a left atrium LA, and a left ventricle LV. During normal operation of the heart 10, deoxygenated blood from the body is returned to the right atrium RA from the superior vena cava 12 and inferior vena cava 14. The right atrium RA pumps the blood through the atrioventricular or tricuspid valve 16 to the right ventricle RV, which then pumps the blood through the pulmonary valve 18 and the pulmonary artery 20 to the lungs for reoxygenation and removal of carbon dioxide. The newly oxygenated blood from the lungs is transported to the left atrium LA, which pumps the blood through the mitral valve 22 to the left ventricle LV. The left ventricle LV pumps the blood through the aortic valve 24 and the aorta 26 throughout the body.

FIG. 2 is another schematic cutaway view of the heart 10 showing a location of the bundle of His 30 in the heart. The bundle 30 consists of fast-conducting muscle fibers that begin at the atrioventricular node in the right atrium and pass to the interventricular septum. The bundle 30 divides in the septum into a right branch that travels along the right side of the septum and supplies excitation to the right ventricle, and a pair of left branches that travel along the left side of the septum and supply excitation to the left ventricle. The fibers in the branches terminate in an extensive network of Purkinje fibers which distribute excitation pulses to the layer of cells beneath the endocardium.

Returning to FIG. 1, the IMD 50 includes a pulse generator 52 that is operably coupled to an implantable lead 54 through a lead adaptor 56. The lead adaptor 56 is configured to receive a lead connector (not shown) of the lead 54. Although the IMD 50 includes only one lead in FIG. 1, a number of other leads (e.g., two, three, four, etc.) may be used. The lead 54 is designed to penetrate the endocardium in contact with His bundle 30. The lead 54 may enter the vascular system through one of several possible vascular access sites and extends through the superior vena cava 12 to the right atrium RA.

In FIG. 1, the IMD 50 is a cardiac pacemaker. In other embodiments, however, the IMD 50 may include an ICD, a CRT-D, an ICD coupled with a pacemaker, and the like. The IMD 50 may be a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto. The IMD 50 may be controlled to sense atrial and ventricular waveforms of interest, discriminate between two or more ventricular waveforms of interest, deliver stimulus pulses or shocks, and inhibit application of a stimulation pulse to a heart based on the discrimination between the waveforms of interest and the like.

Although not shown, the IMD 50 may wirelessly communicate with an external device. For example, the external device may initiate the pulse generator 52. The external device and the pulse generator may communicate identification data (e.g., obtain model and serial number) between one another. The external device may generate a chart that correlates to the patient having the pulse generator 52. The external device may instruct the pulse generator 52 to perform an electrode integrity check and measure parameters of the electrodes (e.g., impedance of shock electrode(s)). The external device and/or the pulse generator may determine a sensing configuration for the pulse generator based on cardiac activity. During initiation of the pulse generator 52, therapy parameters may be selected by the user of the external device.

Figure 3:
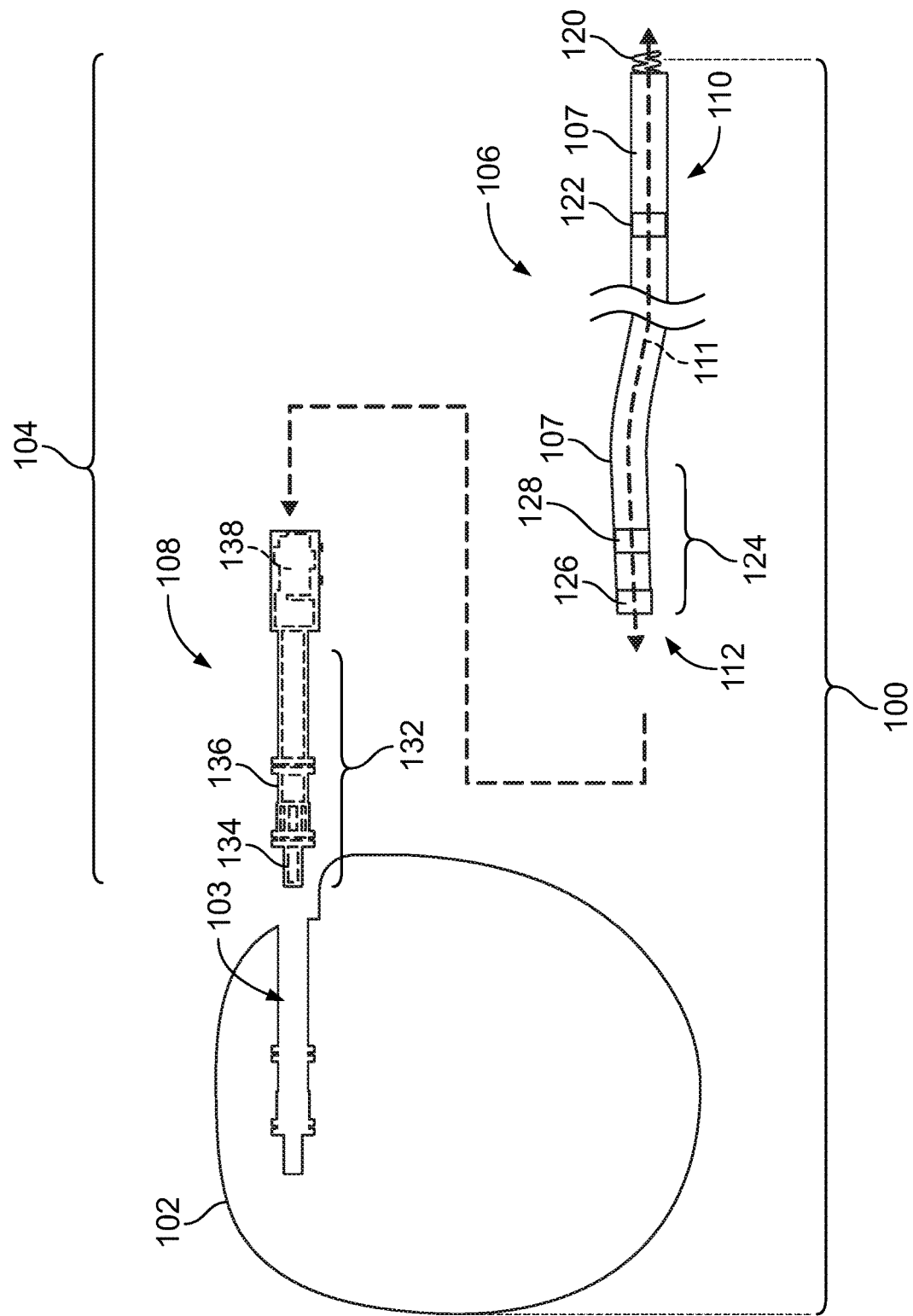
FIG. 3 is a schematic diagram of an IMD formed in accordance with an embodiment that includes an implantable lead, a lead adaptor, and a pulse generator.

FIG. 3 is a schematic diagram of a system 100, which is hereinafter referred to as an implantable medical device (IMD) 100. The IMD 100 is not assembled in FIG. 3. In some embodiments, the IMD 100 may be grouped or packaged as a set or kit. The IMD 100 includes an implantable pulse generator 102 and a lead assembly 104. The pulse generator 102 has a connector cavity 103 that is configured to mate with the lead assembly 104. The lead assembly 104 includes an implantable lead 106 and a lead adaptor 108. The lead 106 includes a lead body 107 that extends lengthwise along a longitudinal axis 111 between a distal end 110 and a proximal end 112. The term longitudinal axis encompasses both linear and non-linear axes. For example, the longitudinal axis 232 111 may extend along a curved path that changes as the lead body 107 is flexed, bent, twisted, or otherwise manipulated.

The lead 106 includes a plurality of electrodes 120, 122 positioned at the distal end 110. The electrodes 120, 122 are arranged in a bipolar configuration but other configurations may be used. The lead 106 also has a lead connector 124 positioned at the proximal end 112. The lead connector 124 includes a portion of the lead body 107 and lead contacts 126, 128 that are communicatively coupled to the electrodes 120, 122 through a plurality of conductors (not shown) that are contained within the lead body 107. In the illustrated embodiment, the lead body 107 is iso-diametric such that a diameter of the lead 106 is essentially uniform throughout. The iso-diametric body 107 may permit an introducer sheath (not shown) to slide over the lead connector 124 when the introducer sheath is removed.

Various combinations of the electrodes and contacts may be used in connection with sensing cardiac signals and/or delivering stimulation therapies. For example, the electrodes 120, 122 include a tip electrode 120 and a ring electrode 122, and the lead contacts 126, 128 include a tip contact 126 and a ring contact 128. In other embodiments, however, the electrodes and contacts may include any number of electrodes/contacts and have a variety of types or shapes.

As described herein, the lead body 107 may have a body outer envelope that is configured to fit within a lumen of an introducer sheath and the lead connector 124 has a connector outer envelope configured to fit within the lumen of the introducer sheath. The lead body 107 includes an insulating sheath or housing of a suitable insulative, biocompatible, biostable material such as, for example, silicone rubber or polyurethane, extending substantially the entire length of the lead body and surrounding the conductors.

The lead adaptor 108 is configured to interconnect the implantable lead 106 and the pulse generator 102. As shown, the lead adaptor 108 has an insertable connector 132 that includes mating contacts 134, 136. The lead adaptor 108 also includes and an adaptor cavity 138 that includes cavity contacts. The cavity contacts are positioned to engage the lead contacts 126, 128 of the lead connector 124 when the lead connector 124 is inserted into the adaptor cavity 138 of the lead adaptor 108. The insertable connector 132 is configured to be inserted into the connector cavity 103 of the pulse generator 102.

Figure 4:
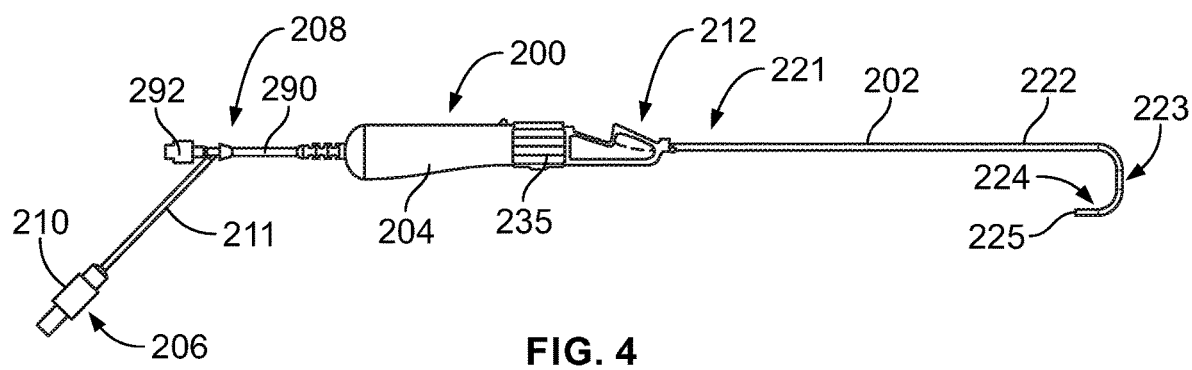
FIG. 4 is a side view of a delivery system formed in accordance with an embodiment.

FIG. 4 is a side view of a delivery system 200 formed in accordance with an embodiment. The delivery system 200 includes an introducer sheath 202, a handle 204, a connector assembly 206, and a fluid flushing assembly 208. Each of these components is described in greater detail in U.S. application Ser. No. 16/452,223, filed on Jun. 25, 2019 (now U.S. Pat. No. 11,413,454, issuing Aug. 16, 2022), which is incorporated herein by reference in its entirety.

Figure 6:
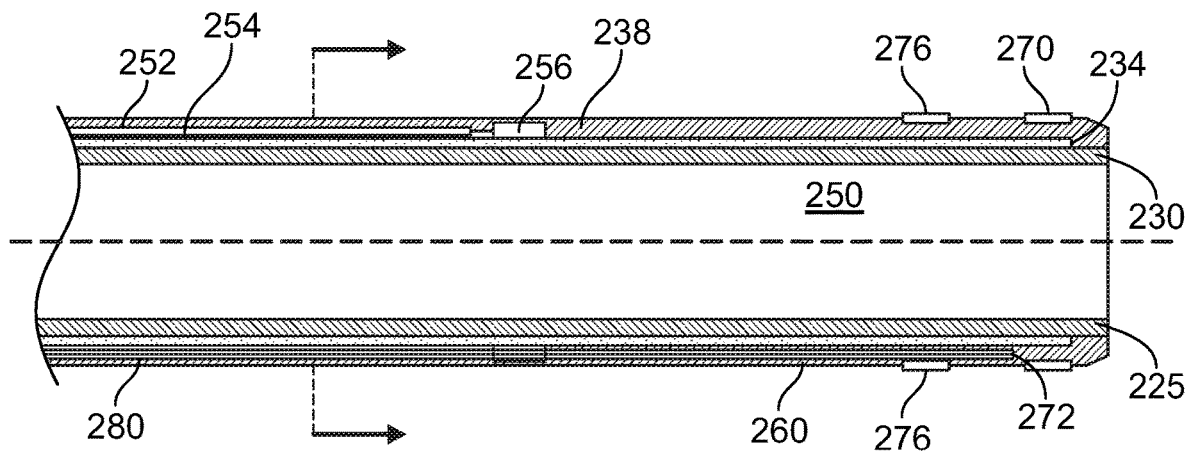
FIG. 6 is a longitudinal cross-section of the introducer sheath of FIG. 5.
Figure 7:
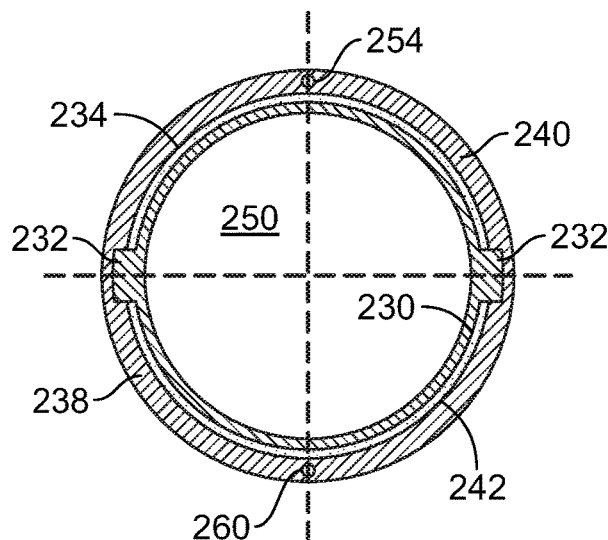
FIG. 7 is a transverse cross-section of the introducer sheath of FIG. 5.

The connector assembly 206 includes an electrical connector 210 coupled to a trailing end of handle 204. The electrical connector 210 is electrically coupled to one or more electrodes along the introducer sheath 202. In the illustrated embodiment, the electrical connector 210 is communicatively coupled to electrodes 270, 272 (FIG. 6) and optionally an electrode 274 (FIG. 6) through conductors 280 that are embedded within the introducer sheath 202. The connector assembly 206 is configured to communicatively couple to an electrogram mapping system (not shown).

The handle 204 may include a hemostasis hub 212 for accepting and coupling to (e.g., tethering to) a proximal end of the introducer sheath 202. The introducer sheath 202 has a sheath lumen 250 (FIG. 6) through which an implantable lead, such as the implantable lead 106 (FIG. 3), may be inserted. The hemostasis hub 212 includes an entrance that permits access to the sheath lumen 250. The fluid flushing assembly 208 is also configured to mechanically couple to the hemostasis hub 212 and fluidly couple to the sheath lumen 250 through the hemostasis hub 212.

The introducer sheath 202 is configured to introduce a lead into a designated anatomical region (e.g., a patient's heart). To this end, the introducer sheath 202 may include a plurality of sheath segments or portions. For example, the introducer sheath 202 may include a proximal segment 221, a body segment 222, a deflectable segment 223, and a distal end segment 224 having an atraumatic distal tip 225. Based on its intended use, the introducer sheath 202 may be configured to exhibit various properties. For example, the introducer sheath may be maneuverable and have a sufficient columnar strength for being inserted through a tortuous vascular system. The introducer sheath may also have sufficient kink-resistance so as to bend smoothly. Multiple layers of the introducer sheath may be configured to have these and other properties.

Figure 5:
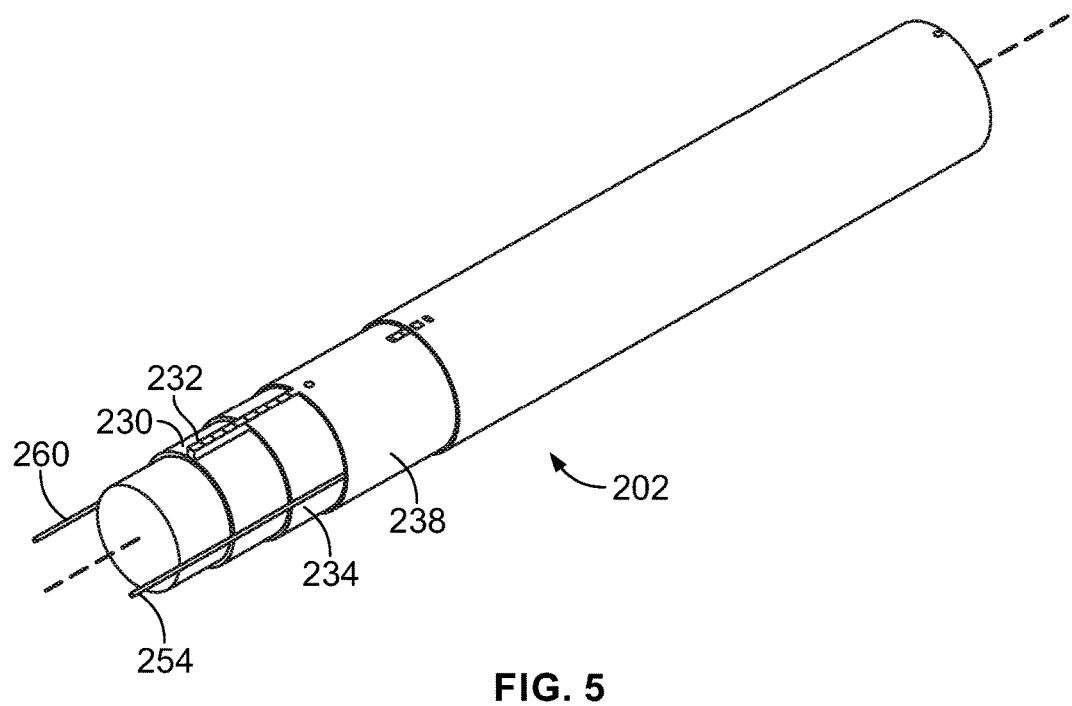
FIG. 5 is a perspective view of a portion of an introducer sheath in accordance with an embodiment and illustrates different layers of the introducer sheath.

FIG. 5 illustrates multiple layers the that introducer sheath 202 may have. For example, the introducer sheath 202 includes an inner layer 230 or liner of the introducer sheath 202. The inner layer 230 may be formed from a tube of a lubricious material to facilitate the passage of the implantable lead, such as the implantable lead 106 (FIG. 3), and also rotation of the lead within the introducer sheath, such as when the lead is rotated to affix the distal end to cardiac tissue. One example of a lubricious material for forming the inner layer 230 includes polytetrafluoroethylene (PTFE).

Optionally, the inner layer 230 may include at least one rib or wedge 232 that protrudes radially from the outer surface of the inner layer 230. The rib 232 may extend entirely or nearly entirely from the proximal end to the distal end of the introducer sheath 202. In the illustrated embodiment, the inner layer 110 includes two ribs 232 that extend substantially parallel to one another on diametrically opposed surfaces of the inner layer 230. In other embodiments, however, the introducer sheath 202 does not include (or is devoid of) the ribs 232.

As an example, the inner layer 230 may be formed from a free-flowing fine powder form of PTFE mixed with a lubricant, such as a hydrocarbon fluid, including, but not limited to, Naphtha solvents, $C_9$-$C_{15}$ hydrocarbons or isoparaffinic hydrocarbons, or mineral spirits to create a paste. One or more particulate ingredients may be added to the paste, including radiopaque fillers, such as barium sulfate, inorganic pigments, and/or reinforcing nanoclay particles. The paste may be compression-molded into a preform of an appropriate shape, such as a hollow or solid cylinder. The preform may then be formed into the tubular inner layer 230 using a paste or ram extrusion process. Following extrusion, the inner layer 230 may be subjected to a series of processing ovens at sequentially increasing temperatures to flash off the lubricants and to partially or completely sinter (or thermally fuse) the PTFE powder particles. By ram extruding the PTFE paste at high pressures, the PTFE powder particles will form platelet-like fibrils oriented in the axial or extrusion direction. Optionally, the outer surface of the inner layer 230 is chemically activated through physical and/or chemical surface treatment methods, including chemical plasma treatment or chemical etching processes known in the art.

In some embodiments, the introducer sheath 202 may include a braided layer 234 disposed over the inner layer 230 to enhance its columnar and torsional strengths of the introducer sheath 203. The braided layer 234 may include a plurality of metallic braids impregnated with one or more thermoplastic polymers. Examples of acceptable thermoplastic polymers include polyamides, such as nylon 11, nylon 12, nylon 612, and the like; polyesters, such as polybutylene terephthalate), poly(ethylene terephthalate), and the like; and thermoplastic elastomers, such as poly (ether-block-amide) copolymer resins, poly(ether-co-ester) block copolymer resins, and various thermoplastic polyurethane block copolymer resins. The thermoplastic polyurethane block copolymer resins can have different hard and soft segment chemistries, including, but not limited to, polyether-based aromatic or aliphatic polyurethanes, polyester-based aromatic or aliphatic polyurethanes, polycarbonate-based aromatic and aliphatic polyurethanes, silicone-containing polyether-based aromatic or aliphatic polyurethanes, silicone-containing polycarbonate-based aromatic or aliphatic polyurethanes, or any combinations thereof.

Optionally, the braided layer 234 may include two C-shaped sections 240 and 242 in which each of the sections 240, 242 is positioned on each side of the two ribs 232. The sections 240, 242 may extend along an entire length of the introducer sheath 202 or may extend only through the proximal segment 221 and the body segment 222. Methods of forming the braided layer 234, as well as other layers of the introducer sheath, are described in greater detail in U.S. application Ser. No. 16/452,223, filed on Jun. 25, 2019 (now U.S. Pat. No. 11,413,454, issuing Aug. 16, 2022) which is incorporated herein by reference in its entirety.

The introducer sheath 202 also includes an outer layer 238 disposed over the C-shaped sections 240 and 242 of the braided layer 234. The outer layer 238 extends along an entire length of introducer sheath 202 and may provide or enhance the columnar strength in the proximal segment 221 and the body segment 222 and permit the deflectable segment 223 to be flexible. The outer layer 238 may be formed from different polymers capable of being extruded to desired dimensions and capable of providing desired properties.

The sheath lumen 250 extends continuously through introducer sheath 202 along its entire length. The sheath lumen 250 may have a diameter that is slightly larger than the diameter of the implantable lead to be delivered to the heart by delivery system 200. For example, the sheath lumen 250 may have a size of about 7.5 French (a diameter of about 2.5 mm) to accommodate a 7 French implantable lead (having a diameter of about 2.33 mm).

The introducer sheath 202 may also include a pull wire 252 that extends through a wall of the introducer sheath 202. For example, the pull wire 252 may extend through a tube 254 extending along the length of the introducer sheath 202 between the braided layer 234 and the outer layer 238. As another example, the tube 254 may be positioned between the inner layer 230 and the braided layer 234. The tube 254 may be formed from a material that will resist collapsing or kinking during the manufacture of the introducer sheath 202 and the use of the delivery system 200. Optionally, the tube 254 may include metal braids to further enhance its kink resistance.

The pull wire 252 may be welded or otherwise affixed at its distal end to a pull wire retainer 256 and may be connected at its proximal end to an operating mechanism in the handle 204. The pull wire retainer 256 may be axially located in the distal end segment 224 of the introducer sheath 202 and fixed (e.g., embedded) in place between the braided layer 234 and the outer layer 238 or between the inner layer 230 and the braided layer 234. In the illustrated embodiment, the pull wire retainer 256 is a ring embedded within the introducer sheath 202, but the pull wire retainer 256 may have other shapes or configurations (e.g., C-shaped segment).

The distal end segment 224 of the introducer sheath 202 may also include one or more electrodes. For example, the distal end segment 224 includes a pair of split-mapping electrodes 270 and 272. The electrodes 270 and 272 are electrically connected to connector assembly 206 via electrical conductors 280. Any suitable material, such as platinum-iridium, may be used to form the electrodes 270 and 272. In the illustrated embodiment, the electrodes 270, 272 are diametrically opposed to one another on opposite sides of the introducer sheath 202. Optionally, the electrodes 270, 272 may be spaced apart in the circumferential direction by, for example, between about 1 mm and about 3 mm.

The electrical conductor 280 may extend from each of electrodes 270 and 272 through a narrow tube 260 extending along the length of the introducer sheath 202 between the braided layer 234 and the outer layer 238 or between the inner layer 230 and the braided layer 234. The tube 260 may be formed from the same polymer used to form the tube 132 and may optionally include metal braids to enhance kink resistance. Upon exiting the tube 260, the electrical conductors 280 may travel through a lumen (not shown) in the handle 204 and through a conduit 211 to an electrical connector 210 (FIG. 3).

In the illustrated embodiment, the electrodes 270 and 272 are split-mapping electrodes and do not fully circumscribe the introducer sheath 202. The electrodes 270, 272 may be secured to the introducer sheath 202 so as to not become detached therefrom upon advancement of the introducer sheath 202 through the patient's vascular system to deliver the implantable lead to the bundle of His 30 or during removal of the introducer sheath from the patient following such procedure. Accordingly, while the electrodes 270 and 272 may be positioned at the tip of the distal end of the introducer sheath 202 to thereby be exposed on the distal end face of the introducer sheath 202, the electrodes 270, 272 may be spaced from the tip so as to be surrounded on all sides by a continuous mass of the sheath polymer.

The electrodes 270 and 272 may be positioned based on the direction in which the distal tip of the introducer sheath deflects. For example, the electrodes may be positioned so that, when the introducer sheath is deflected, the electrodes are generally aligned in the direction in which the fibers of the bundle of His are oriented. A maximum signal will be detected from the bundle of His when both the electrode 270 and the electrode 272 are located directly thereover. More specifically, if the electrodes 270 and 272 are oriented on opposite sides of a deflection plane when the introducer sheath 202 is deflected, only one electrode at a time will be able to be located over the bundle of His 30. As introducer sheath 202 is moved relative to the atrial septal wall in an area in close proximity to the His bundle, one electrode may move closer to the His bundle while the other electrode may move away from the His bundle, such that the maximum possible signal will not be obtained. On the other hand, by positioning both of electrodes 270 and 272 in the deflection plane, both electrodes can lie over the bundle of His 30 at the same time. In fact, as introducer sheath 202 is moved across the atrial septal wall, there will be a distance equal to about the diameter of the introducer sheath within which the maximum His bundle signal can be detected.

The handle 204 may also include a conduit 290 having a connector 292 at a proximal end of the handle 204 for connecting to a source of flushing fluid. The conduit 290 may be connected to a further conduit (not shown) that travels through the handle 204 to hub 212 for supplying the flushing fluid to flush the interior of the introducer sheath 202. The conduit 211, having the electrical conductors 280 extending therethrough, may be connected at one end to the conduit 290 by a Y-splitter, and at the other end may be connected to the electrical connector 210. The electrical conductors 280 travel from the electrodes 270 and 272 through narrow tubes 260 and through the handle 204 and exit therefrom through the conduits 290 and 211, and are then connected by soldering or the like to the electrical connector 210.

Figure 8:
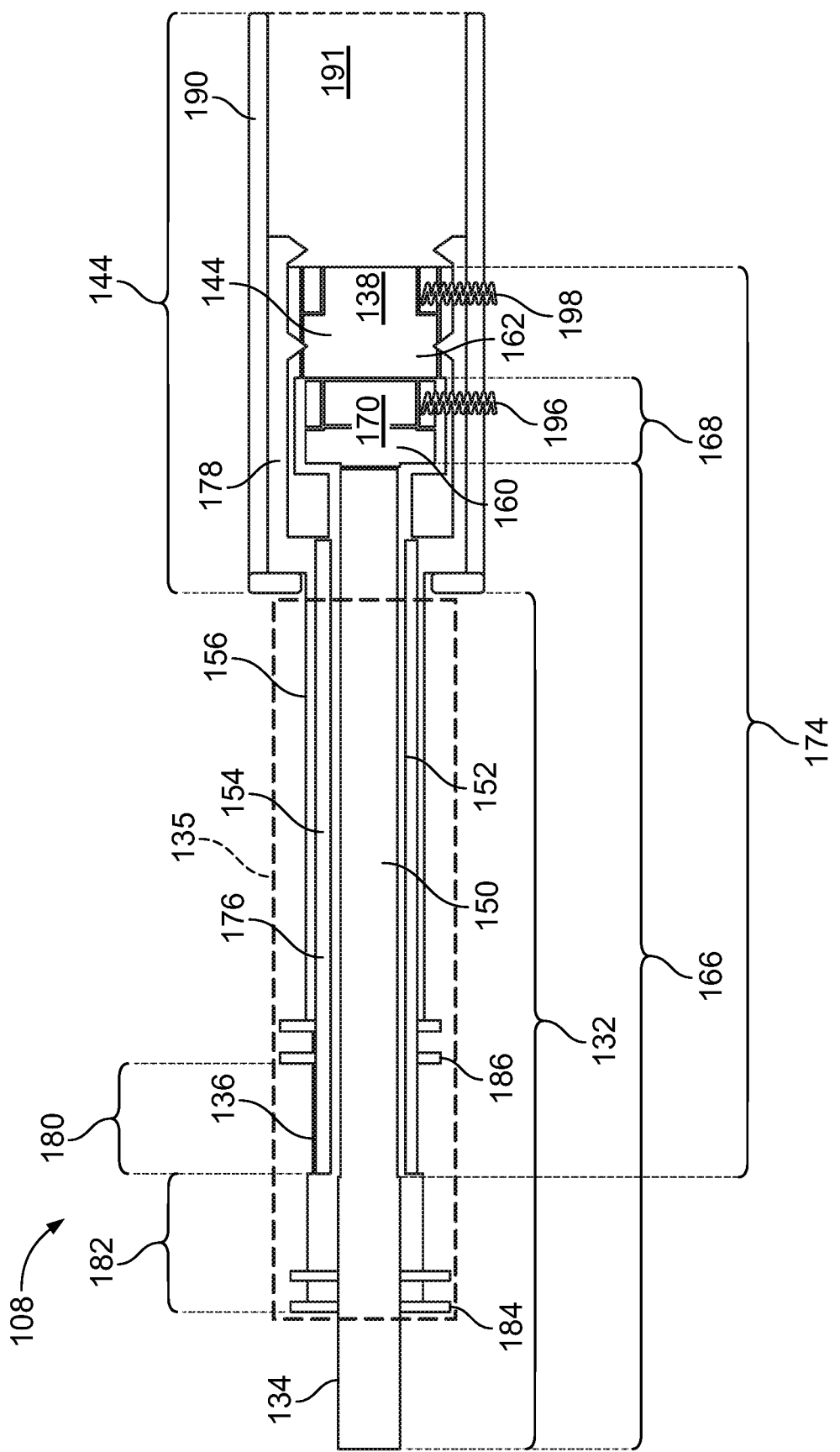
FIG. 8 is a longitudinal cross-section of the lead adaptor of FIG. 3 in accordance with an embodiment that is configured to interconnect the pulse generator and the implantable lead.

FIG. 8 is a longitudinal cross-section of the lead adaptor 108. The insertable connector 132 (or device-engaging portion) is configured to mechanically and electrically couple to the pulse generator 102 (FIG. 3). The lead adaptor 108 also includes a receptacle connector 144 (or lead-engaging portion). In the illustrated embodiment, the receptacle connector 144 includes the adaptor cavity 138 and is configured to mechanically and electrically couple to the implantable lead 106 (FIG. 3). As such, the lead adaptor 108 interconnects the pulse generator 102 and the lead 106 and effectively changes a size of the lead connector 124 (FIG. 3).

In the illustrated embodiment, the insertable connector 132 and the receptacle connector 144 have fixed positions with respect to each other and directly couple to each other. In other embodiments, an intermediate portion (not shown) of the lead adaptor 108 may extend between and join the insertable connector 132 and the receptacle connector 144, thereby increasing a length of the lead assembly 104 (FIG. 3). In such embodiments, the lead adaptor 108 may also be referred to as a lead extender or lead extension.

As shown in FIG. 8, the body of the lead adaptor 108 essentially includes a first conducting portion 150, a first insulating portion 152, a second conducting portion 154, and a second insulating portion 156. The first conducting portion 150 electrically couples a first cavity contact 160 to the mating contact 134, which may also be referred to as the first mating contact 134. In the illustrated embodiment, the first cavity contact 160 and the first mating contact 134 are respective surfaces of the first conducting portion 150. In other embodiments, however, at least one of the first cavity contact 160 or the first mating contact 134 are surfaces of discrete conductive elements that form a conductive pathway. More specifically, the first conducting portion 150 may include multiple discrete conductive elements.

The first conducting portion 150 includes a pin extension 166 and a barrel section 168 that defines a receiving hole 170. The pin extension 166 projects in an axial direction away from the barrel section 168. The receiving hole 170 is an opening or space that is sized to receive the lead contact 126 (FIG. 3). As used herein, the phrases "[feature] that is sized to" or "[feature] sized to" or similar phrase means the feature has a size (e.g., dimensions) for a certain purpose. The phrases do not refer to a manufacturing step or operation.

The first insulating portion 152 surrounds the first conducting portion 150 and electrically isolates the first conducting portion 150 and the second conducting portion 154 from each other. The second conducting portion 156 also includes a pin extension 176 and a barrel section 178. However, the second conducting portion 156 includes a bore 174 that extends through the second conducting portion 156. A portion of the bore 174 receives the pin extension 166 of the first conducting portion 150 and the first insulating portion 152 surrounding the pin extension 166. Another portion of the bore 174 receives the barrel section 168 of the first conducting portion 150 and the first insulating portion 152 surrounding the barrel section 168. In the illustrated embodiment, the first insulating portion 152 is a single layer molded around the first conducting portion 150. In other embodiments, however, especially for those in which the first conducting portion 150 has multiple elements, the first insulating portion 152 may have multiple layers or multiple discrete sections.

The second insulating portion 156 is sized to cover a majority of an outer surface of the second conducting portion 154, except for an exposed area 180. The exposed area 180 may represent the second mating contact 136. The first insulating portion 152 may be sized to provide a leading flange 182. The leading flange 182 separates an end of the second conducting portion 154 from the first mating contact 134 of the first conducting portion 150. In the illustrated embodiment, the first and second insulating portions 152, 156 are shaped to include sealing rings 184, 186, respectively. Again, although the first and second insulating portions are each shown as a separate single continuous part, each of the first and second insulating portions may include multiple parts. This may also be characterized as having more insulating portions (e.g., third insulating portion, fourth insulating portion, etc.).

Also shown, the lead adaptor 108 may include one or more fasteners for securing the lead connector 124 (FIG. 3) to the lead adaptor 108. For example, the lead adaptor 108 may include set screws 196, 198. The set screw 196 engages the lead contact 126 and presses the lead contact 126 against the first cavity contact 160 so that a sufficient electrical connection is established. Likewise, the set screw 198 engages the lead contact 128 and presses the lead contact 128 against a second cavity contact 162 so that a sufficient electrical connection is established.

When fully constructed, the lead adaptor 108 or a portion of the lead adaptor 108 may essentially match a unified or industry standard. For example, the lead adaptor 108 is configured to match the IS-1 standard for bipolar low-voltage/pacing applications. In other embodiments, however, the lead adaptor 108 may be configured to match other unified or industry standards or to have non-standard designs.

In some embodiments, the insertable connector 132 is configured to match a unified or industry standard for being inserted into the connector cavity 103 (FIG. 3), and the receptacle connector 144 is configured to match a unified or industry standard for mating with the lead connector 124. Other portions of a lead adaptor, however, may not match a unified or industry standard, such as an intermediate portion that effectively increases a length of the lead adaptor.

The lead adaptor 108 effectively increases a size of the lead connector 124, which may be referred to as "upsizing." More specifically, the lead connector 124 is now usable because it can be electrically connected to the pulse generator 102. In other embodiments, the lead adaptor 108 may effectively decrease the size of the lead connector (downsize) or, yet in other embodiments, may not change a size of the lead connector.

The insertable connector 132 of the lead adaptor 108 has an insertable envelope 135. As used herein, an "envelope" represents a three-dimensional space that can be occupied by an element. The insertable envelope 135 of the insertable connector 132 may be larger than the sheath lumen 250 (FIG. 5) of the introducer sheath 202 (FIG. 4) such that the insertable connector 132 is not capable of readily sliding through the sheath lumen 250. For example, the insertable connector 132 may have a dimension (e.g., diameter or radius) that is greater than a diameter or radius of the sheath lumen.

The adaptor cavity 138 is defined by multiple elements. For example, the adaptor cavity 138 includes the hole 170 and a portion of the bore 174. Optionally, the receptacle connector 144 may include a strain-relief segment 190 that is attached to the barrel section 178 of the second conducting portion 154. For example, the strain-relief segment 190 surrounds an end of the barrel section 178. A portion of the strain-relief segment 190 extends beyond an end of the second conducting portion 154 such that the adaptor cavity 138 also includes a cavity portion 191 that is defined by the strain-relief segment 190. The strain-relief segment 190 may comprise a material that is more flexible than the second conducting portion 154.

Figure 9:
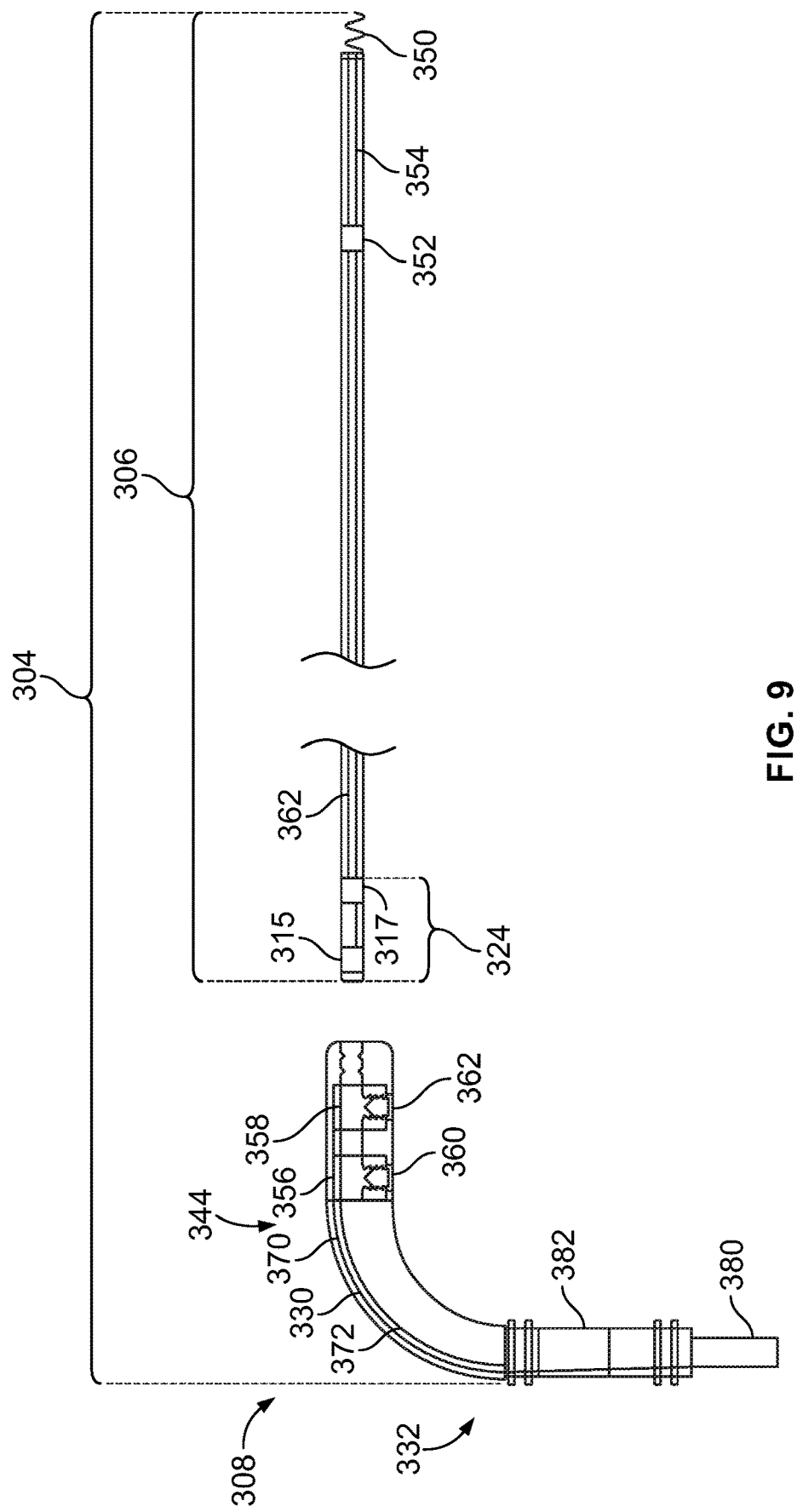
FIG. 9 is a longitudinal cross-section of a lead assembly including an implantable lead and a lead adaptor.

FIG. 9 is a longitudinal cross-section of a lead assembly 304 including an implantable lead 306 and a lead adaptor 308. The lead adaptor 308 may include features that are similar or identical to the features of the lead adaptor 108 (FIG. 3). For example, the lead adaptor 308 may include an insertable connector 332 and a receptacle connector 344. In some embodiments, the lead adaptor 308 may have an intermediate bent section 330 that extends between and joins the insertable connector 332 and the receptacle connector 344. For example, the bent section 330 may enable wrapping the lead assembly 304 around an exterior of the pulse generator (not shown) when implanted in a patient. In some embodiments, the bent section 330 is resilient such that some yielding is permitted. In other embodiments, the bent section 330 is more rigid. Yet still in other embodiments, the bent section 300 is flexible such that the bent section 330 may be bent or twisted into a variety of positions.

As shown, the implantable lead 306 includes a fixation anchor 350 that is configured to engage a secure the distal end to tissue, such as the bundle of His. The fixation anchor 350 may constitute a first electrode of the implantable lead 306 and is illustrated as a helical screw. The implantable lead 306 also includes a second electrode 352, which is shown as a ring electrode in the illustrated embodiment. In some embodiments, the second electrode 352 may function as an anode and the first electrode 350 may function as a cathode. As shown, an electrical conductor 354 electrically connects the first electrode 350 to a lead contact 315 at a proximal end of the lead 306. An electrical conductor 362 electrically connects a lead contact 317 to the second electrode 352.

A portion of the implantable lead 306 forms a lead connector 324 that includes the lead contacts 315, 317 that is insertable into the receptacle connector 344. The receptacle connector 344 includes a connector block 356 and a connector block 358. The connector blocks 356, 358 align with and electrically couple to the lead contacts 315, 317, respectively. Fasteners 360, 362 are positioned adjacent to self-sealing septa that engage the lead connector 324 and urge the lead connector 324 against the receptacle connector 344, thereby establishing an electrical connection between the connector block 356 and the lead contact 315 and the connector block 358 and lead contact 317.

The lead adaptor 308 includes an electrical conductor 370 that communicatively couples the connector block 356 to a mating contact 380 and also includes an electrical conductor 372 that communicatively couples the connector block 358 to a mating contact 382. The insertable connector 332 of the lead adaptor 308 may be consistent with a predetermined standard, such as IS-1. The receptacle connector 344 may also be consistent with a predetermined standard.

Figure 10:
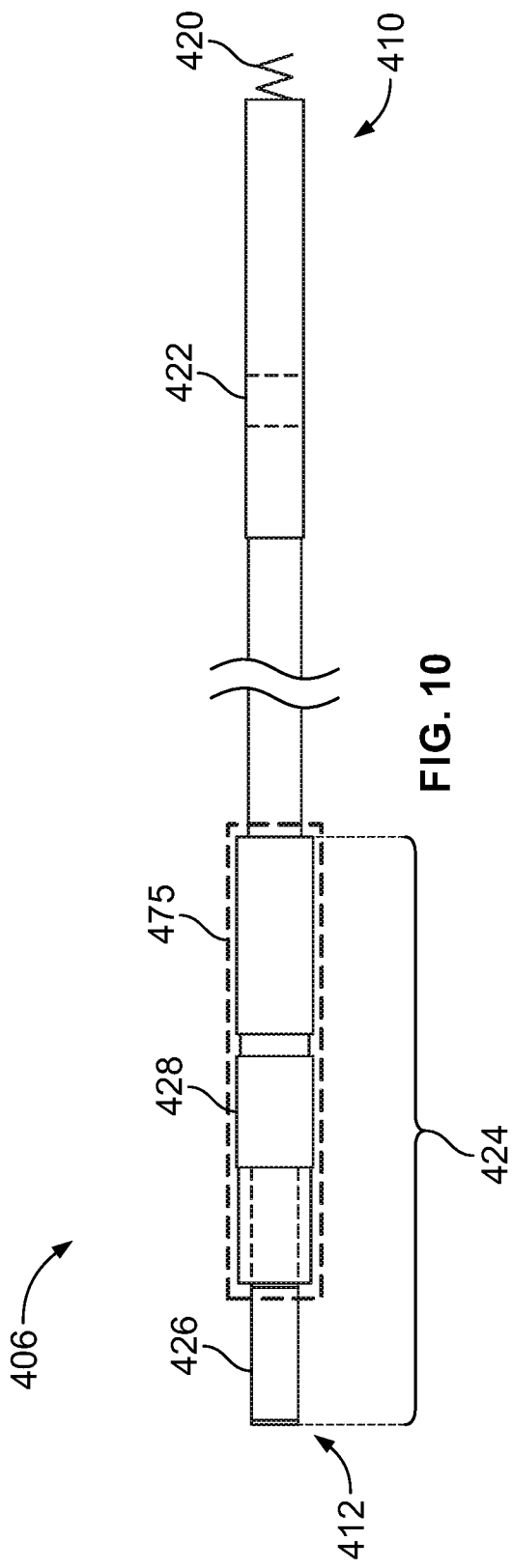
FIG. 10 is a side view of an implantable lead in accordance with an embodiment.
Figure 11:
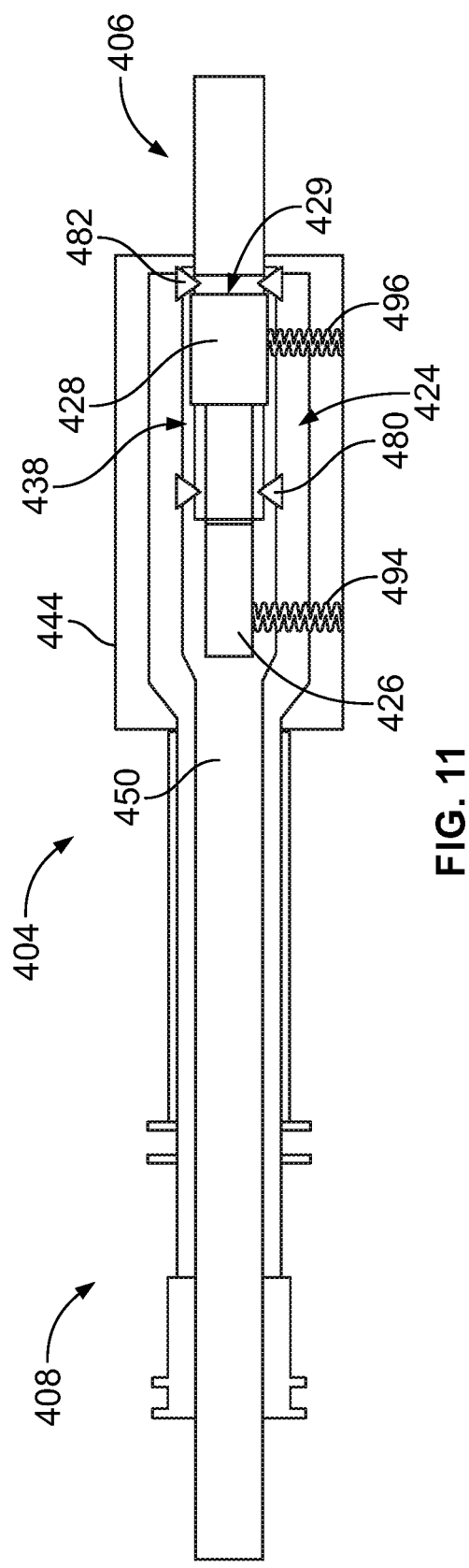
FIG. 11 is a longitudinal cross-section of a lead adaptor in accordance with an embodiment that is configured to interconnect the implantable lead of FIG. 10 and a pulse generator.

FIG. 10 is a side view of an implantable lead 406 formed in accordance with an embodiment. The implantable lead 406 may have features that are similar or identical to the implantable lead 106 (FIG. 3) and is configured to mechanically and electrically couple to a lead adaptor 408 (FIG. 11). For example, the lead 406 includes a lead body 407 that extends lengthwise along a longitudinal axis between a distal end 410 and a proximal end 412. The lead 406 includes a plurality of electrodes 420, 422 positioned at the distal end 410. The electrodes 420, 422 are arranged in a bipolar configuration but other configurations may be used.

The lead 406 also has a lead connector 424 positioned at the proximal end 412. The lead connector 424 includes a portion of the lead body 407 and lead contacts 426, 428 that are communicatively coupled to the electrodes 420, 422 through a plurality of conductors (not shown) that are contained within the lead body 407. The lead connector 424 may size and configured to be similar to an IS-1 connector or another unified or industry standard. However, the lead connector 424 is devoid of sealing rings that project radially away from an outer surface of the lead connector 424. The sealing rings may be effectively replaced by interior ridges of the lead adaptor 408.

FIG. 11 is a longitudinal cross-section of a lead assembly 404 that includes the implantable lead 406 and the lead adaptor 408. The lead adaptor 408 may include features that are similar or identical to the features of the lead adaptor 108 (FIG. 3). For example, the lead adaptor 408 includes an insertable connector 432 and a receptacle connector 444. As shown in FIG. 11, the lead connector 424 is mated with the lead adaptor 408 such that the lead connector 424 has been inserted into the adaptor cavity 438. The lead contact 426 is being held against a first conducting portion 450 of the lead adaptor 408 by a set screw 494, and the lead contact 428 is being held against a second conducting portion 454 by a set screw 496.

As shown, the lead adaptor 408 includes a first sealing ridge 480 and a second sealing ridge 482 positioned within the adaptor cavity 438. The first and second sealing ridges 480, 482 may extend circumferentially around the adaptor cavity 438 and the lead connector 424. The first sealing ridge 480 is positioned to engage an insulating portion 484 of the lead connector 424, thereby electrically isolating the lead contacts 426, 428. The second sealing ridge 482 may engage an insulative outer surface of the lead 406 at a trailing edge 429 of the lead contact 428. By engaging the outer surface of the lead 406 behind the trailing edge 429, the second sealing ridge 482 separates the lead contact 428 from fluid outside of the lead adaptor 408 and stops movement or prevents movement of the lead connector 424 in a withdrawal direction.

Returning to FIG. 10, by removing the sealing rings from the lead connector 424, a connector outer envelope 475 is reduced. An IS-1 connector has a maximum outer diameter that is defined by the sealing rings. The maximum outer diameter is about 12 French (F) (or 4.00 millimeters (mm)), which may require an introducer sheath having a lumen that is at least 13 F (or 4.33 mm). Without the sealing rings, the maximum outer diameter is about 8 F (or 2.67 mm), which may only require a sheath lumen that is 9 F (or 3.00 mm).

Figure 12:
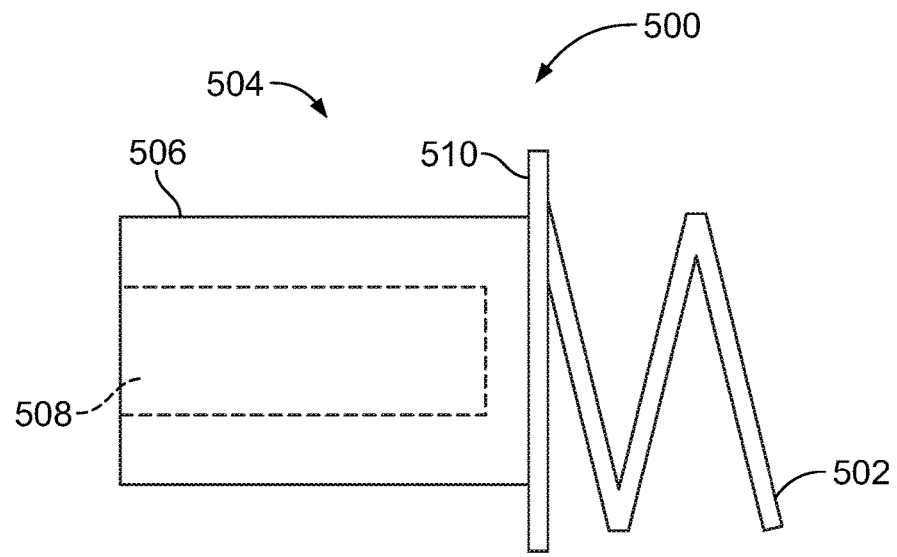
FIG. 12 is a side view of a holding spool formed in accordance with an embodiment that is configured to receiving a holding stylet.
Figure 13:
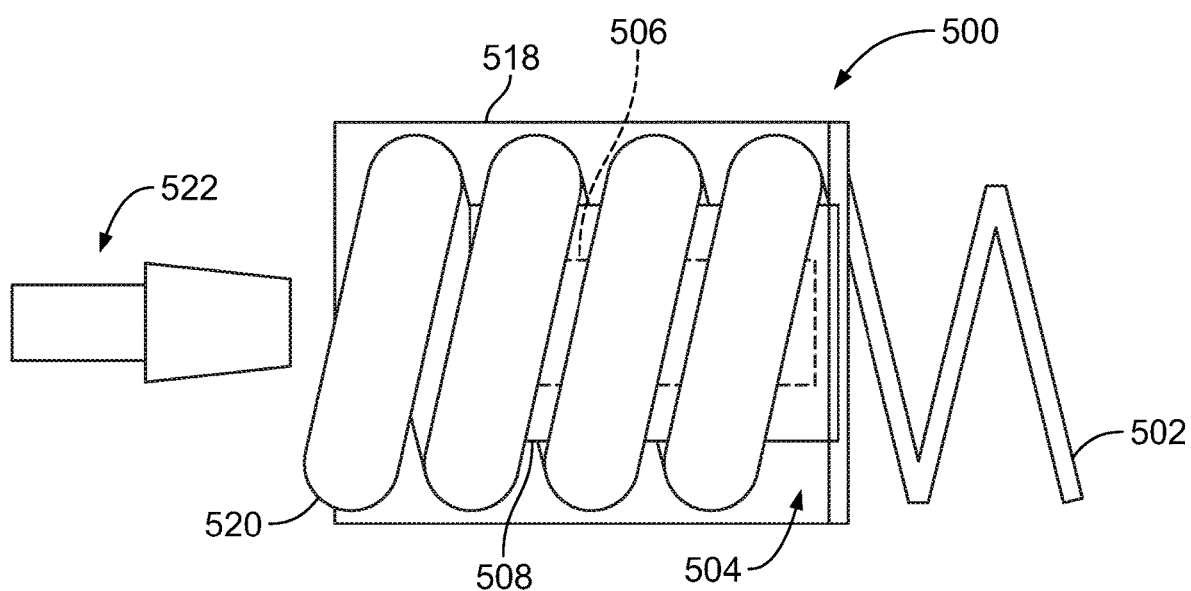
FIG. 13 is a side view of a distal end of an implantable lead that includes the holding spool of FIG. 12.

FIGS. 12 and 13 are side views illustrating elements of a tip assembly 500 that may be positioned at a distal end of an implantable lead, such as the implantable leads 106, 306, and 406 described above. The tip assembly 500 includes a fixation anchor 502 that is secured to an end of a holding spool or cup 504. The holding spool 504 includes a body 506 having an optional recess 508. In the illustrated embodiment, the body 506 is cylindrically-shaped and the recess 508 is positioned to be aligned with a central longitudinal axis (not shown) of the implantable lead and is shaped to receive a single, narrow projection. As shown in FIG. 13, the body 506 is configured to have an electrical conductor 520 wrapped around the body 506, and the recess 508 is shaped to receive a distal end of a holding stylet 522.

In other embodiments however, the body 506 may have other shapes, such as having an octagonal cross-section, rectangular cross-section, or triangular cross-section that is taken transverse to the longitudinal axis. Likewise, the recess may have another location and/or shape. For example, the recess may be cross-shaped or may be configured to receive multiple fingers or projections of the holding stylet.

In some embodiments, the fixation anchor is 502 is helically- or corkscrew-shaped and is secured to a plate or disc 510 that is coupled to the body 506. The fixation anchor 502 is electrically-conductive and comprises a suitable material for the cardiovascular environment (e.g., platinum-iridium). The plate 510 comprises MP35N (e.g., Nickel-Cobalt-Chromium alloy) that is also suitable material for the cardiovascular environment. The fixation anchor 502 may be welded to the plate 510, and the plate 510 may be welded to the body 506. In other embodiments, the holding spool can be machined to include a disc- or plate- shaped top.

The fixation anchor 502 and the plate 510 may constitute the distal tip of the implantable lead. When the lead (not shown) is rotated, the fixation anchor 502 is driven into the tissue (not shown) and the plate 510 is drawn closer to the tissue. The plate 510 may directly face and abut, including contact, the tissue when the fixation anchor 502 is fully embedded.

As shown in FIG. 13, the tip assembly 500 may also include the electrical conductor 520 and an insulative coating 518. The insulative coating 518 may be disposed within outer layers or tubes of the implantable lead. In some embodiments, the insulative coating 518 may form a portion of the distal end of the lead that is exposed to the environment. For example, the insulative coating 518 may form a cylindrical body that is attached to an end of the elongated tubes of the lead body such that the cylindrical body effectively increases a length of the lead. In some cases, the cylindrical body may overlap a portion of the elongated tubes or be molded/shaped at least partially within the ends of the tubes. The insulative coating 518 may comprise, for example, a silicone rubber tubing, polyurethane tubing, or a combination thereof. As another example, the insulative coating 518 may include reflowed polyurethane or a composite copolymer of silicone and polyurethane.

The electrical conductor 520 is electrically coupled to one of the lead contacts (not shown) of the implantable lead. The electrical conductor 520, the body 506, and the plate 510 are portions of a common conductive pathway that is configured for at least one of pacing or sensing electrical activity of the heart. As described below, when the optional recess 508 is utilized, a holding stylet 522 may be inserted into the recess 508 to hold the distal end of the lead in position as the introducer sheath is withdrawn.

Figure 14:
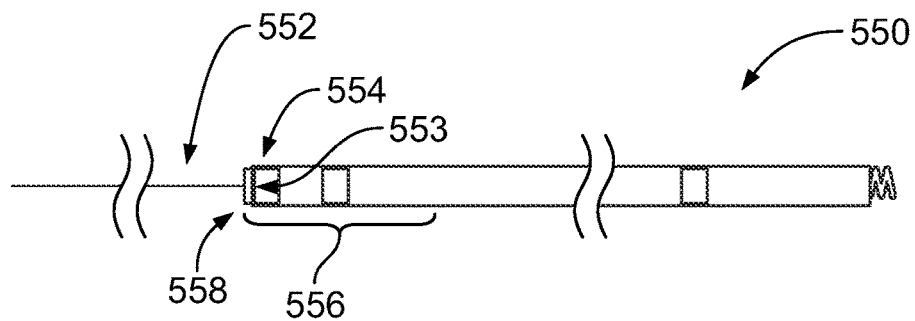
FIG. 14 illustrates a holding stylet that is configured to engage a proximal end of an implantable lead formed in accordance with an embodiment.

FIG. 14 is a side view of an implantable lead 550, which may include features that are similar or identical to the features of other implantable leads described herein, such as the implantable leads 106, 306, and 406 described above. In particular embodiments, the implantable lead 550 is a lumen-less lead. Lumen-less leads enable using introducer sheaths having a smaller diameter. As shown, a holding stylet 552 is engaged to a tip 554 of a lead connector 556 at a proximal end 558 of the lead 550. The holding stylet 552 may have stylet face 553 that engages the tip 554. The stylet face 553 may have an area or profile that is smaller than a cross-sectional profile of the lumen and, optionally, smaller than a profile of the tip 554 of the lead connector 556. As described below, the holding stylet 552 may engage the proximal end 558 or the lead connector 556 to hold the distal end of the implantable lead 550 in position as the introducer sheath is withdrawn. In some embodiments, the holding stylet 552 may be similar to a plunger that grips the proximal end 558 or the lead connector 556.

Figure 16:
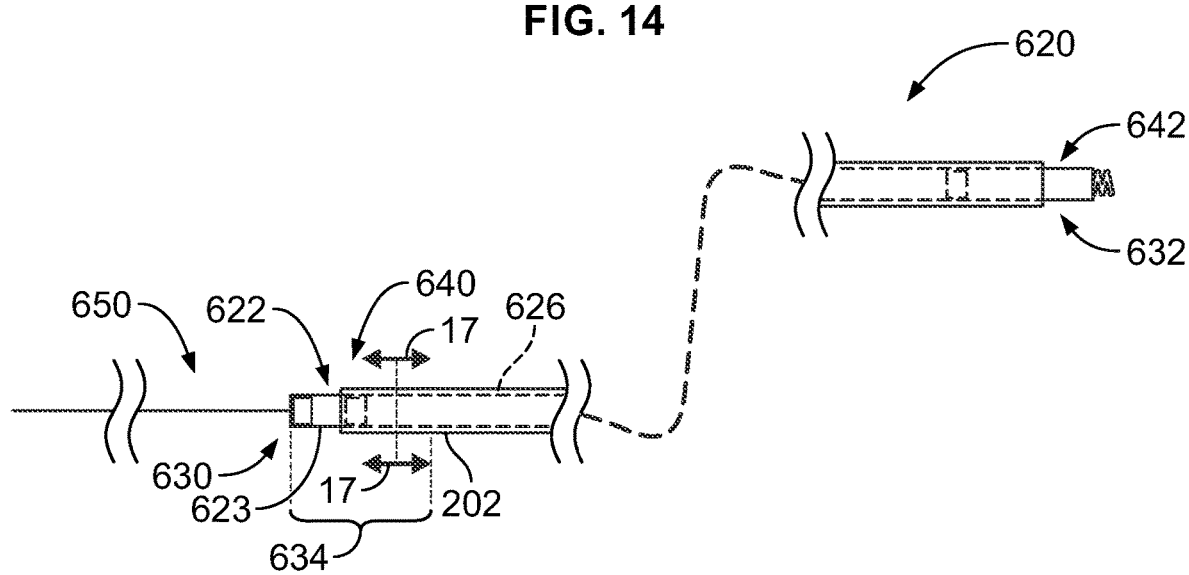
FIG. 16 illustrates an implantable lead disposed within an introducer sheath formed in accordance with an embodiment.
Figure 15:
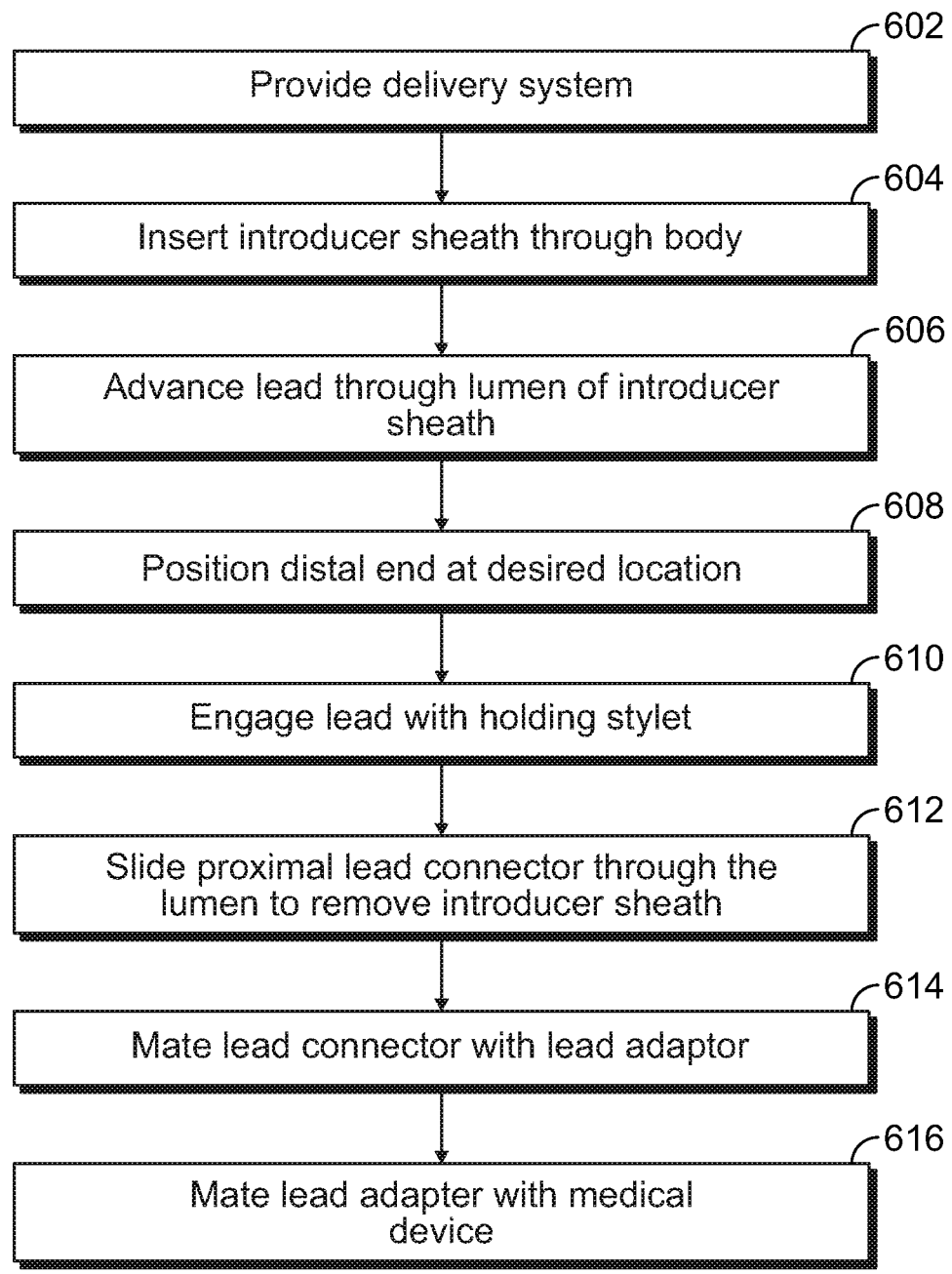
FIG. 15 is a block diagram of a method in accordance with an embodiment.

FIG. 15 is a flowchart illustrating a method 600 of positioning an implantable lead with respect to cardiac tissue. The method 600 is described with reference to FIGS. 16-20. FIG. 16 shows a working assembly 600 having the introducer sheath 202 and an implantable lead 622 disposed within a lumen 626 of the introducer sheath 202. The lead 622 may be similar or identical to other leads described herein. The lead 622 includes a lead body 623 having a proximal lead end 630 and a distal lead end 632. As shown, at least a portion of the proximal lead end 630 is clear (or extends beyond) a proximal sheath end 640 of the introducer sheath 202, and at least a portion of the distal lead end 632 of the lead 622 clears a distal sheath end 642 of the introducer sheath 202.

Also shown in FIG. 16, a holding stylet 650 is operably engaged with the lead 622. For example, the holding stylet 650 may be similar to the holding stylet 522 (FIG. 13) and be engaged with a holding spool of a tip assembly, such as the holding spool 504 (FIG. 12) of the tip assembly 500 (FIG. 12). Alternatively, the holding stylet 650 may be similar to the holding stylet 552 (FIG. 14) and be engaged with the proximal end 630 of the lead 622 (or a lead connector 634).

Figure 17A:
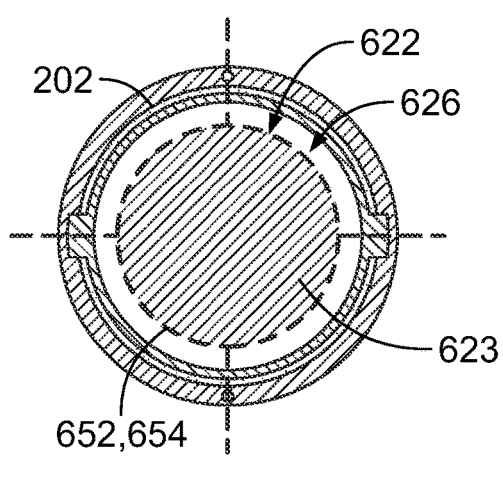
FIG. 17A is a cross-section of the introducer sheath of FIG. 16 having the implantable lead disposed therein.

FIG. 17A is a cross-section of the working assembly 620 taken along the lines 17-17 in FIG. 16 and illustrates a cross-sectional profile of the lead 622 at the axial location identified by the lines 17-17. As shown, the lead body 623 has a body outer envelope 652 (indicated by the bolded dashed-lines) that is sized to fit within the lumen 626 of the introducer sheath 202. The lead connector 634 (FIG. 16) also has a connector outer envelope 654 that is configured to fit within the lumen 626 of the introducer sheath 202. In the illustrated embodiment, the lead 622 is an iso-diametric lead such that the lead body 623 and the lead connector 634 have essentially a common (or the same) cross-sectional profile throughout a length of the lead 622. As such, each of the body outer envelope 652 and the connector outer envelope 654 is configured to fit within the lumen 626 of the introducer sheath 202 such that the lead 622 and the introducer sheath 202 may slide relative to each other without damaging the lead 622 for an entire length of the introducer sheath 202.

As used herein, a "cross-sectional profile" includes the outer surface (or outline) of an elongated instrument at a certain axial location of the elongated instrument. An outer envelope (e.g., of a lead body or a lead connector), on the other hand, may include an axial segment or portion of the lead. The outer envelope may account for localized features along that segment of the lead that extend radially outward, such as sealing rings or portions of an electrical contact, or biased segments or kinks in the lead. For example, a length of the outer envelope may be determined by the length of the designated lead segment (e.g., length of the lead connector) and the two-dimensional cross-section of this outer envelope may be determined by the maximum cross-sectional profile along this designated lead segment. For embodiments in which the lead 622 is iso-diametric, a cross-sectional profile and an outer envelope can be the same.

Figure 17B:
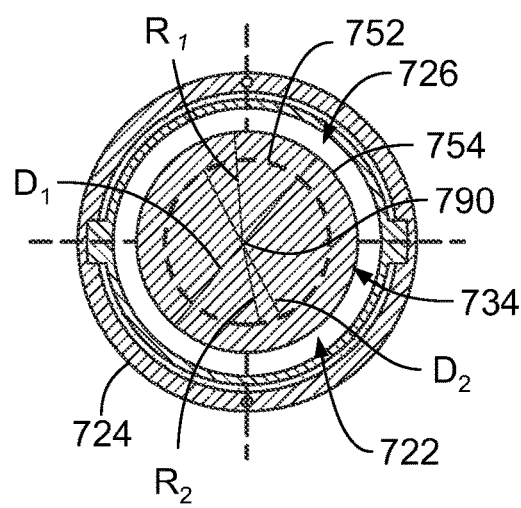
FIG. 17B is a cross-section of the introducer sheath of FIG. 16 having a different implantable lead disposed therein.

FIG. 17B illustrates a cross-section of a different lead 722 having a lead body 723. The lead 722 may include features that are similar or identical to the features of the lead 406 (FIG. 10) in which portions of a lead connector 734 are larger than portions of the lead body 723 extending between the distal and proximal ends of the lead 722. A body outer envelope 752 of the lead body 723 is identified by a dashed circle, and a connector outer envelope 754 of the lead connector 734 is identified by a larger dashed circle that forms an outline of the lead 722 in FIG. 17B.

As shown, the body outer envelope 752 and the connector outer envelope 754 are defined by respective dimensions. For example, a dimension of the connector outer envelope 754 may be a diameter $D_1$ that intersects a central longitudinal axis 790 of the lead 722. The dimension of the connector outer envelope 754 may also be a radius $R_1$ that projects from the central longitudinal axis 790 to the outer surface. Similarly, a dimension of the body outer envelope 752 may be a diameter $D_2$ that intersects the central longitudinal axis 790 of the lead 722. The dimension of the body outer envelope 752 may also be a radius $R_2$ that projects from the central longitudinal axis 790.

The connector outer envelope 754 is configured to fit within the lumen 726 of the introducer sheath 724 for an entire length of the introducer sheath 724. The introducer sheath 724 may be similar or identical to the introducer sheath 202 (FIG. 4). Likewise, the body outer envelope 752 is configured to fit within the lumen 726 of the introducer sheath 724 for an entirety of the introducer sheath 724. In particular embodiments, the body outer envelope 752 is defined by a body dimension (e.g., $D_2$ and/or $R_2$) and the connector outer envelope 754 is defined by a connector dimension (e.g., $D_1$ and/or $R_1$). The body dimension is not greater than the connector dimension. In other embodiments, the body dimension may be greater than the connector dimension. In other embodiments, the body dimension and the connector dimension are essentially equal.

Figure 18:
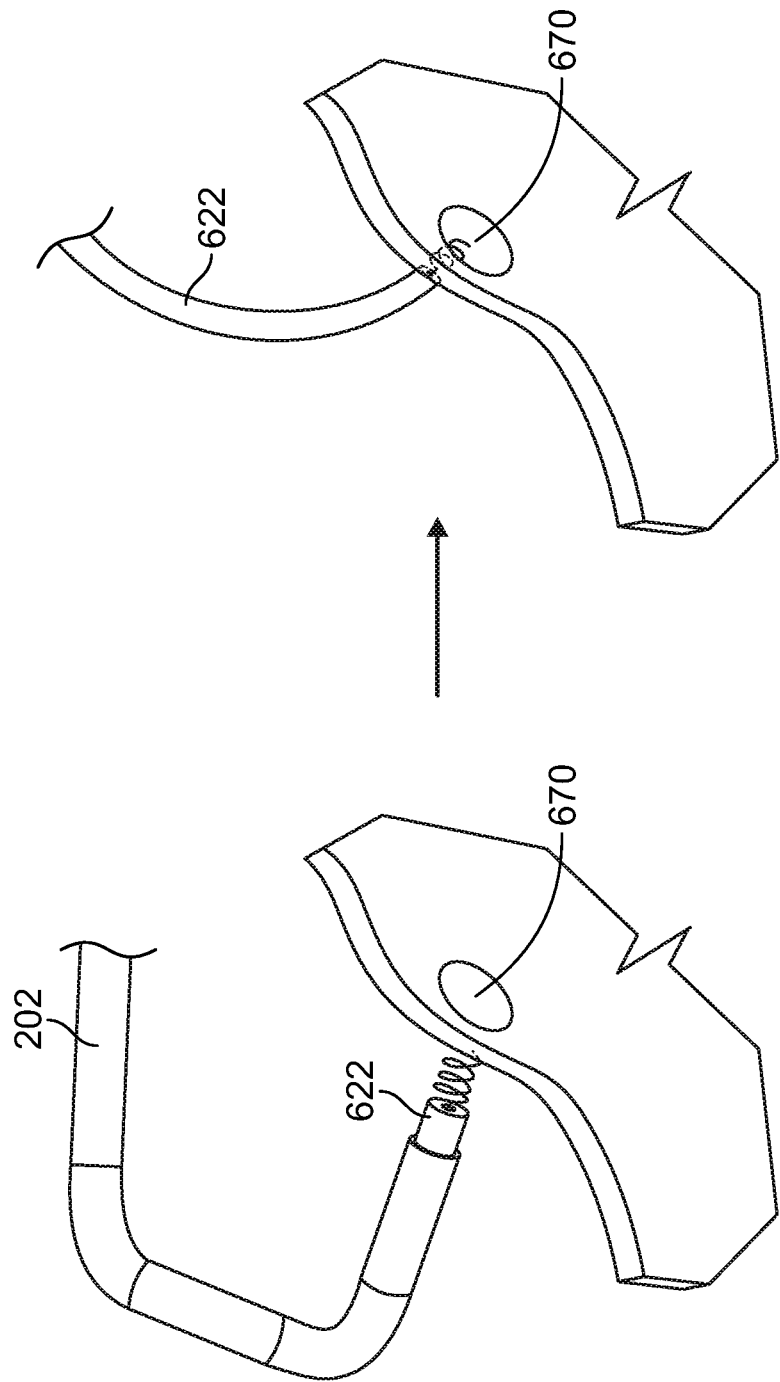
FIG. 18 illustrates the use of a delivery system for capturing the His bundle with an implantable lead.

Returning to FIG. 15, the method 600 will be described in relation to using the delivery system 200 to deliver and affix the implantable lead 622 (FIG. 16) to a bundle of His 670 (FIG. 18). It should be understood, however, that other embodiments described herein may be used when implementing the method 600 and also that the method 600 may be suitable for other procedures in which a predetermined location in the body is targeted. It should also be understood that other delivery systems may be used when implementing the method 600.

At 602, the delivery system 200 is provided. As described above, the delivery system 200 includes the introducer sheath 202, the handle 204 (FIG. 4), a connector assembly 206 (FIG. 4), and a fluid flushing assembly 208 (FIG. 4). At 604, the introducer sheath 202 is inserted through an access point (not shown) into the vascular system. The access point may be created by a needle (not shown) that is inserted into the vascular system prior to the introducer sheath. The introducer sheath 202 may then use the needle as a guide through the access point and into the vascular system.

With a mapping device (not shown) coupled to the electrodes 270, 272 (FIG. 6) through the connector assembly 204, the introducer sheath 202 is directed into the superior vena cava and is maneuvered through the superior vena cava to the right atrium. During this insertion procedure, the introducer sheath 202 of the delivery system may have a substantially straight configuration and may include a dilator (not shown) positioned in the lumen of the introducer sheath 202 to enlarge the access path and to provide support to the introducer sheath 202 as it is being maneuvered. The straight configuration of the introducer sheath 202 facilitates its passage through the superior vena cava and into the right atrium. Once the distal tip 225 of the introducer sheath 202 has entered the right atrium, the dilator may be removed from the delivery system and the implantable lead 622 may be inserted into the sheath lumen 250, at 606.

With the distal portion of the introducer sheath 202 fully within the right atrium, the implanter may operate the delivery system 200 to place the introducer sheath 202 in a deflected configuration. Deflecting the introducer sheath 202 may be accomplished by an actuator 235 (FIG. 4) that is operably coupled to the sheath segments 221-223. With the proximal section 221 of the introducer sheath 202 positioned in the superior vena cava and the deflectable section 223 of the introducer sheath 202, the distal tip 225 of the introducer sheath 202 will point generally toward the region in the atrial septum at which the bundle of His 670 is located, and will be in close proximity to the septum. If electrical signals are received from the electrodes 270 and 272 in this position of the introducer sheath 202, the implanter will know that the distal tip 225 of the introducer sheath 202 is aligned with the His bundle 670.

If the electrodes 270, 272 are not receiving electrical signals, or if the signals are very faint, the implanter may maneuver the distal tip 225 of the introducer sheath 202 by small movements of the actuator 235 in either a forward or reverse direction to scan the atrial wall. These small movements of actuator 235 will deflect the deflectable section 223 of the introducer sheath 202 by small amounts toward or away from the proximal section 221 of the introducer sheath 202. The His bundle 670 is located when the signals received by the electrodes 270, 272 are strongest.

Once this mapping procedure has located the bundle of His, the distal end 632 of the implantable lead 622 can be secured to the desired location, at 608. More specifically, the implantable lead 622 can be secured to the His bundle by advancing a fixation anchor 680 out from the distal tip 225 of the introducer sheath 202 and rotating the implantable lead 622 within delivery system 200 to drive the fixation anchor 680 into the atrial septal wall.

Once the implantable lead 622 has been properly fixed to the tissue including the bundle of His 670, the introducer sheath 202 may be returned to a substantially straight configuration by rotating the actuator 235 in the direction opposite that used for deflection. The introducer sheath 202 may then be removed from around the lead 622. Optionally, at 610, a holding stylet 692 may operably engage the implantable lead 622 at the tip assembly or at a tip of the lead connector, thereby holding the implantable 622 in a substantially stationary position while the introducer sheath 202 is withdrawn. As described herein, the introducer sheath 202 may be withdrawn without splitting, peeling, or otherwise separating the introducer sheath 202 into sections.

Figure 19:
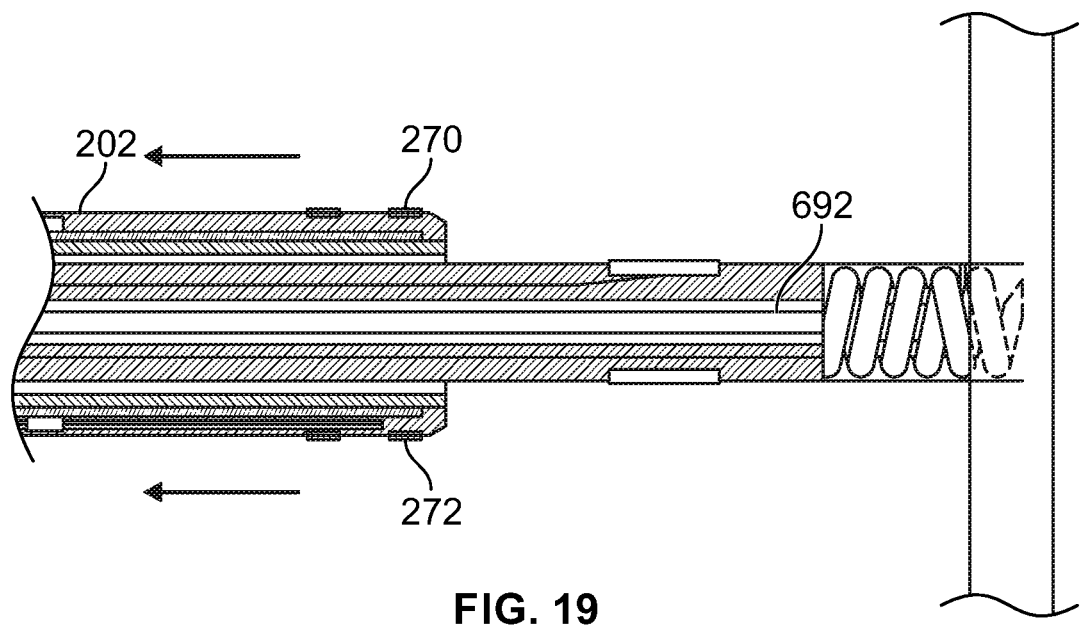
FIG. 19 is a longitudinal cross-section of the introducer sheath sliding over the implantable lead using a holding stylet in accordance with an embodiment.
Figure 20:
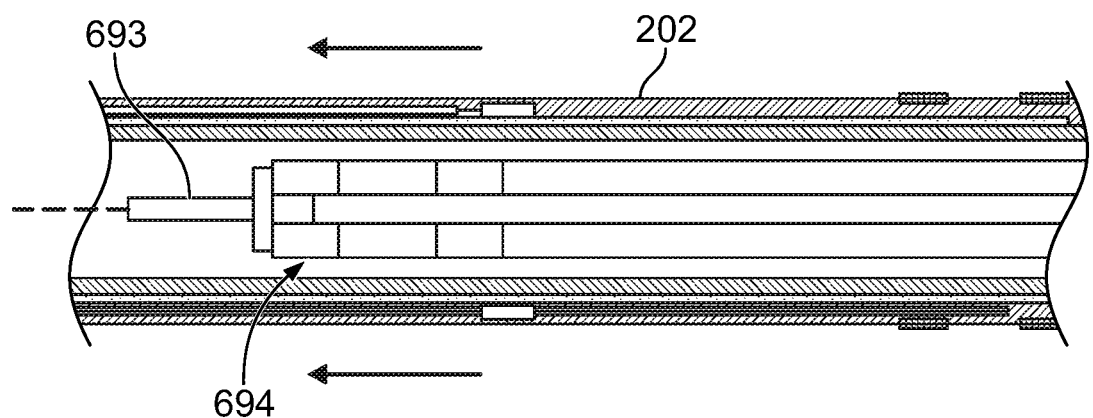
FIG. 20 is a longitudinal cross-section of the introducer sheath sliding over the implantable lead using a different holding stylet in accordance with an embodiment.

FIG. 19 illustrates the holding stylet 692 engaging a tip assembly of the implantable lead 622. In such embodiments, the holding stylet 692 may be, for example, at least about two times (2×) as long as the introducer sheath 202. In an alternative embodiment shown in FIG. 20, a holding stylet 693 may be used to engage a proximal end 694 of a lead. In such embodiments, the holding stylet 692 may be, for example, at least equal to a length of the introducer sheath 202.

With the implantable lead 622 operably engaged by a holding stylet (e.g., either of the holding stylets 692, 693), the holding stylet reduces the likelihood that the implantable lead 622 will be excessively moved or dislodged by the introducer sheath 202 as the introducer sheath 202 is withdrawn. Because the body outer envelope and the connector outer envelope of the implantable lead 622 fit within the sheath lumen 250, the introducer sheath 202 may slide over the entire implantable lead 622. For embodiments that include the holding stylet 692, the introducer sheath 202 may be completely removed because the length of the holding stylet 692 is at least about 2× the length of the introducer sheath 202. For embodiments that include the holding stylet 693, the introducer sheath 202 may be completely removed because the length of the holding stylet 693 is at least equal to the length of the introducer sheath 202. After the distal tip of the introducer sheath 202 clears the proximal end of the implantable lead 622, the introducer sheath 202 is removed, at 612.

At 614, the lead connector of the implantable lead 622 may be mated with a lead adaptor. Optionally, the lead adaptor may include a strain-relief segment that extends beyond an end of the body of the lead adaptor. At 616, the lead adaptor may then be mated with the medical device. In particular embodiments, the lead adaptor may include an insertable connector having an insertable outer envelope that is larger than the lumen of the introducer sheath.

It will be readily understood that the components of the embodiments as generally described and illustrated in the Figures herein, may be arranged and designed in a wide variety of different configurations in addition to the described example embodiments. Thus, the more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

What is claimed is:
1. A system comprising:
an introducer sheath having a lumen, the sheath configured to be introduced through a vascular system into a chamber of a heart, the sheath having one or more closed layers that entirely surround the lumen and extend along a length of the sheath;
an implantable lead comprising a lead body having a distal end and a proximal end, the implantable lead having electrodes positioned at the distal end and having a lead connector positioned at the proximal end, the lead connector including lead contacts that are communicatively coupled to the electrodes positioned at the distal end, wherein the lead body has a body outer envelope that fits within the lumen of the introducer sheath and the lead connector has a connector outer envelope that fits within the lumen of the introducer sheath such that the sheath is configured to slide over the lead connector when the sheath is removed;
a pulse generator having a connector cavity; and a lead adaptor configured to interconnect the implantable lead and the pulse generator, the lead adaptor having an insertable connector that includes mating contacts and an adaptor cavity that includes cavity contacts, wherein the cavity contacts are positioned to engage the lead contacts of the lead connector when the lead connector is inserted into the adaptor cavity, wherein the insertable connector is configured to be inserted into the connector cavity of the pulse generator.

2. The system of claim 1, wherein the body outer envelope is defined by a first dimension and the connector outer envelope is defined by a second dimension that is not greater than the first dimension.

3. The system of claim 1, wherein the body outer envelope is defined by an outer radius extending from a central longitudinal axis to an outer surface of the lead body.

4. The system of claim 1, wherein the insertable connector has an insertable outer envelope that is larger than the lumen of the introducer sheath.

5. The system of claim 1, further comprising the introducer sheath, the lead connector and the distal end of the lead body being slidable within the lumen of the introducer sheath.

6. The system of claim 5, further comprising low-friction material disposed between an interior surface of the introducer sheath and the lead body.

7. The system of claim 1, wherein the lead adaptor has an adaptor body and a strain-relief segment coupled to a receiving end of the adaptor body, the adaptor body and the strain-relief segment defining respective portions of the adapter cavity, the strain-relief segment configured to at least partially resist bending forces delivered by the implantable lead.

8. The system of claim 1, wherein the lead body includes a fixation anchor attached to the distal end and configured to be implanted within tissue, the system further comprising a holding stylet configured to engage the lead body when the introducer sheath is withdrawn and diminish withdrawing forces that pull the fixation anchor away from the tissue.

9. The system of claim 1, wherein the distal end is configured to penetrate an endocardium in contact with a HIS bundle and the lead connector fits within the lumen of the introducer sheath in order for the introducer sheath to be withdrawn over the proximal end of the lead body while the distal end remains in contact with the HIS bundle.

10. The system of claim 1, wherein the introducer sheath and the distal end of the implantable lead are configured to be inserted through a vascular access site into a chamber of the heart.

11. The system of claim 10, wherein the lumen of the introducer sheath has a diameter of about 2.5 mm and the connector outer envelope has a diameter of no more than 2.33 mm.

12. A system comprising:
an introducer sheath having a lumen, the sheath configured to be introduced through a vascular system into a chamber of a heart, the sheath having one or more closed layers that entirely surround the lumen and extend along a length of the sheath;
an implantable lead comprising a lead body having a distal end and a proximal end, the implantable lead having electrodes positioned at the distal end and having a lead connector positioned at the proximal end, the lead connector including lead contacts that are communicatively coupled to the electrodes positioned at the distal end, wherein the lead body has a body outer envelope that fits within the lumen of the introducer sheath and the lead connector has a connector outer envelope that fits within the lumen of the introducer sheath such that the sheath is configured to slide over the lead connector when the sheath is removed;
a lead adaptor configured to interconnect the implantable lead and a pulse generator, the lead adaptor having an insertable connector that includes mating contacts and an adaptor cavity that includes cavity contacts, wherein the cavity contacts are positioned to engage the lead contacts of the lead connector when the lead connector is inserted into the adaptor cavity, wherein the insertable connector is configured to be inserted into a connector cavity of the pulse generator.

13. The system of claim 12, wherein the body outer envelope is defined by a first dimension and the connector outer envelope is defined by a second dimension that is not greater than the first dimension.

14. The system of claim 12, wherein the body outer envelope is defined by an outer radius extending from a central longitudinal axis to an outer surface of the lead body.

15. The system of claim 12, wherein the insertable connector has an insertable outer envelope that is larger than the lumen of the introducer sheath.

16. The system of claim 15, wherein the lead body has a lumen, a holding stylet configured to be inserted through the lumen of the lead body and engage an interior of the lead body at or near the distal end.

17. The system of claim 12, wherein the proximal and distal ends of the lead body are slidable within the lumen of the introducer sheath.

18. The system of claim 17, further comprising low-friction material disposed between an interior surface of the introducer sheath and the lead body.

19. The system of claim 12, wherein the lead adaptor has an adaptor body and a strain-relief segment coupled to a receiving end of the adaptor body, the adaptor body and the strain-relief segment defining respective portions of the adapter cavity.

20. The system of claim 12, wherein the lead body includes a fixation anchor attached to the distal end and configured to be implanted within tissue, the system further comprising a holding stylet configured to engage the lead body when the introducer sheath is withdrawn and diminish withdrawing forces that pull the fixation anchor away from the tissue.

21. The system of claim 12, wherein the lead body is a lumen-less lead body, a holding stylet configured to engage the proximal end of the lead body.

22. The system of claim 12, wherein the distal end is configured to penetrate an endocardium in contact with a HIS bundle and the lead connector fits within the lumen of the introducer sheath in order for the introducer sheath to be withdrawn over the proximal end of the lead body while the distal end remains in contact with the HIS bundle.

23. The system of claim 12, wherein the introducer sheath and the distal end of the implantable lead are configured to be inserted through a vascular access site into a chamber of the heart.

24. The system of claim 23, wherein the lumen of the introducer sheath has a diameter of about 2.5 mm and the connector outer envelope has a diameter of no more than 2.33 mm.

* * * * *